US012692512B2

(12) United States Patent (10) Patent No.: US 12,692,512 B2
Tipper et al. (45) Date of Patent: Jul. 28, 2026

(54) METHODS AND COMPOSITIONS FOR TREATING GLYCOGEN STORAGE DISEASES

(71) Applicant: Ultragenyx Pharmaceutical Inc., Novato, CA (US)

(72) Inventors: Christopher Tipper, Cambridge, MA (US); Kelly Reed Clark, Westerville, OH (US); Samuel Wadsworth, Shrewsbury, MA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 1313 days.

(21) Appl. No.: 17/311,869

(22) PCT Filed: Dec. 18, 2019

(86) PCT No.: PCT/US2019/067247
§ 371 (c)(1),
(2) Date: Jun. 8, 2021

(87) PCT Pub. No.: WO2020/132115
PCT Pub. Date: Jun. 25, 2020

(65) Prior Publication Data
US 2022/0017922 A1 Jan. 20, 2022

Related U.S. Application Data

(60) Provisional application No. 62/781,380, filed on Dec. 18, 2018.

(51) Int. Cl.
*C12N 15/86* (2006.01)
*A61K 38/00* (2006.01)
(Continued)

(52) U.S. Cl.
CPC .............. *C12N 15/86* (2013.01); *C12N 9/16* (2013.01); *C12N 15/11* (2013.01);
(Continued)

(58) Field of Classification Search
CPC ........ C12Y 301/03; C12N 15/11; C12N 9/16; C12N 15/86
See application file for complete search history.

(56) References Cited

U.S. PATENT DOCUMENTS

| | | |
|---|---|---|
| 5,387,484 A | 2/1995 | Doany et al. |
| 5,658,785 A | 8/1997 | Johnson |

(Continued)

FOREIGN PATENT DOCUMENTS

| | | |
|---|---|---|
| WO | WO-2003/052051 A2 | 6/2003 |
| WO | WO-2005/033321 A2 | 4/2005 |

(Continued)

OTHER PUBLICATIONS

Lee, Y. M., Pan, C. J., Koeberl, D. D., Mansfield, B. C., & Chou, J. Y. (2013). The upstream enhancer elements of the G6PC promoter are critical for optimal G6PC expression in murine glycogen storage disease type Ia. Molecular genetics and metabolism, 110(3), 275-280. (Year: 2013).*

(Continued)

*Primary Examiner* — Kevin K Hill
*Assistant Examiner* — Allison Marie Johnson
(74) *Attorney, Agent, or Firm* — Antheros Legal Advisors LLP

(57) ABSTRACT

This invention provides a variety of novel adeno-associated virus (AAV) vectors for gene therapy applications in the treatment of glycogen storage disease type 1a (GSD-Ia). Disclosed herein are a number of recombinant nucleic acid molecules, vectors and recombinant AAV that incorporate a modified G6PC promoter/enhancer sequence. Utilization of (Continued)

the modified G6PC promoter/enhancer sequence results in enhanced AAV yield and quality when expressed from various host cell platforms. Also provided herein are compositions comprising the novel AAV of the invention and methods of treating GSD-Ia using the same.

15 Claims, 9 Drawing Sheets

Specification includes a Sequence Listing.

(51) Int. Cl.
　　*C12N 9/16* (2006.01)
　　*C12N 15/11* (2006.01)
(52) U.S. Cl.
　　CPC ...... *C12Y 301/03009* (2013.01); *A61K 38/00* (2013.01); *C12N 2320/35* (2013.01); *C12N 2750/14143* (2013.01); *C12N 2830/34* (2013.01); *C12N 2830/42* (2013.01); *C12N 2830/50* (2013.01)

(56) References Cited

U.S. PATENT DOCUMENTS

| | | |
|---|---|---|
| 5,688,676 A | 11/1997 | Zhou et al. |
| 5,691,176 A | 11/1997 | Lebkowski et al. |
| 5,741,683 A | 4/1998 | Zhou et al. |
| 5,872,005 A | 2/1999 | Wang et al. |
| 6,004,797 A | 12/1999 | Colosi |
| 6,127,175 A | 10/2000 | Vigne et al. |
| 6,156,303 A | 12/2000 | Russell et al. |
| 6,489,162 B1 | 12/2002 | Shenk et al. |
| 6,566,118 B1 | 5/2003 | Atkinson et al. |
| 6,723,551 B2 | 4/2004 | Kotin et al. |
| 6,753,419 B1 | 6/2004 | Toniatti et al. |
| 6,846,665 B1 | 1/2005 | Horer et al. |
| 6,943,019 B2 | 9/2005 | Wilson et al. |
| 7,271,002 B2 | 9/2007 | Kotin et al. |
| 7,510,872 B2 | 3/2009 | Clark et al. |
| 8,163,543 B2 | 4/2012 | Urabe et al. |
| 8,409,842 B2 | 4/2013 | Clark et al. |
| 8,512,981 B2 | 8/2013 | Hermens et al. |
| 8,980,247 B2 | 3/2015 | Meyers et al. |
| 9,644,216 B2 | 5/2017 | Chou et al. |
| 11,013,774 B2 | 5/2021 | Morrison et al. |
| 2002/0081721 A1 | 6/2002 | Allen et al. |
| 2002/0115189 A1 | 8/2002 | Natsoulis et al. |
| 2002/0127582 A1 | 9/2002 | Atkinson et al. |
| 2004/0235173 A1 | 11/2004 | Bleck et al. |
| 2005/0112765 A1 | 5/2005 | Li et al. |
| 2005/0148076 A1 | 7/2005 | Allen |
| 2006/0013063 A1 | 1/2006 | Singh |
| 2010/0248355 A1 | 9/2010 | Atkinson et al. |
| 2011/0229971 A1 | 9/2011 | Knop et al. |
| 2011/0251547 A1 | 10/2011 | Xing et al. |
| 2012/0058917 A1 | 3/2012 | Gaken et al. |
| 2012/0100606 A1 | 4/2012 | Zolotukhin et al. |
| 2012/0135515 A1 | 5/2012 | Qu et al. |
| 2012/0219528 A1 | 8/2012 | Sista et al. |
| 2013/0072548 A1 | 3/2013 | Wright et al. |
| 2014/0056919 A1 | 2/2014 | Xing et al. |
| 2014/0359799 A1 | 12/2014 | Wang et al. |
| 2015/0024467 A1 | 1/2015 | Sheldon et al. |
| 2015/0353899 A1 | 12/2015 | Pechan et al. |
| 2016/0376608 A1 | 12/2016 | Chou et al. |
| 2017/0362670 A1 | 12/2017 | Chou |
| 2019/0083554 A1 | 3/2019 | Morrison et al. |
| 2019/0290710 A1 | 9/2019 | Jing et al. |
| 2020/0032221 A1 | 1/2020 | Tiernan et al. |
| 2020/0048641 A1 | 2/2020 | Jing et al. |
| 2020/0124505 A1 | 4/2020 | Panteli et al. |
| 2021/0277416 A1 | 9/2021 | Jing et al. |

FOREIGN PATENT DOCUMENTS

| | | | |
|---|---|---|---|
| WO | WO-2014/127196 A1 | 8/2014 | |
| WO | WO-2015081101 A1 * | 6/2015 | ......... A61K 48/0008 |
| WO | WO-2016/106303 A1 | 6/2016 | |
| WO | WO-2017/172772 A1 | 10/2017 | |
| WO | WO-2018/013705 A1 | 1/2018 | |
| WO | WO-2018/071817 A1 | 4/2018 | |
| WO | WO-2018/140946 A1 | 8/2018 | |
| WO | WO-2018/175773 A1 | 9/2018 | |
| WO | WO-2018/175775 A1 | 9/2018 | |
| WO | WO-2018/208960 A1 | 11/2018 | |

OTHER PUBLICATIONS

Miao, Hefan et al. "Long-read sequencing identified a causal structural variant in an exome-negative case and enabled preimplantation genetic diagnosis." Hereditas vol. 155 32. Sep. 28, 2018. (Year: 2018).*
Chen, Ling-Ling, Joshua N. DeCerbo, and Gordon G. Carmichael. "Alu element-mediated gene silencing." The EMBO journal 27.12 (2008): 1694-1705. (Year: 2008).*
Koeberl, Dwight D., et al. "AAV vector-mediated reversal of hypoglycemia in canine and murine glycogen storage disease type Ia." Molecular Therapy 16.4 (2008): 665-672. (Year: 2008).*
Ng et al., Predicting the Effects of Amino Acid Substitutions on Protein Function, Annual Review Genomics Human Genetics 7: 61-80, 2006 (Year: 2006).*
https://www.calculator.net/exponent-calculator.html, last visited Nov. 15, 2024 (Year: 2024).*
Choi et al., "AAV hybrid serotypes: improved vectors for gene delivery," Curr Gene Ther. (2005) vol. 5(3):299-310.
Chou et al., "Glycogen storage disease type I and G6Pase-B deficiency: etiology and therapy." Nat Re. Endocrino. (2010) vol. 6(12):676-88.
Chou et al., "Mutations in the Glucose-6-Phosphatase-a (G6PC) Gene that Cause Type Ia Glycogen Storage Disease," Human Mutation. (2008) vol. 29(7):921-930.
Chou et al., "Recombinant AAV-directed gene therapy for type I glycogen storage diseases," Expert Opinion on Biological Ther. (2011) vol. 11(8):1011-1024.
Clark et al., "Cell lines for the production of recombinant adeno-associated virus", Human Gene Therapy. (1995) vol. 6:1329-1341.
Clark et al., "Highly purified recombinant adeno-associated virus vectors are biologically active and free of detectable helper and wild-type viruses," Hum Gene Ther. (1999) 10(6):1031-1039.
Clark et al., "Recent advances in recombinant adeno-associated virus vector production," Kidney International. (2002) vol. 61, Symposium 1:S9-S15.
Conway et al., "High-titer recombinant adeno-associated virus production utilizing a recombinant herpes simplex virus type I vector expressing AAV-2 rep and cap," Gene Therapy. (1999) vol. 6(6):986-993.
Daya and Berns, "Gene therapy using adeno-associated virus vectors," Clin Microbiol Rev. (2008) vol. 21(4):583-593.
Gao et al., "New recombinant serotypes of AAV vectors," Curr Gene Ther. (2005) vol. 5(3):285-97.
Ghosh et al., "Long-term correction of murine glycogen storage disease type Ia by recombinant adeno-associated virus-1-mediated gene transfer," Gene Ther. (2006) 13(4):321-329.
Howden et al., "The transient expression of mRNA coding for Rep protein from AAV facilitates targeted plasmid integration," J Gene Med. (2008) vol. 10(1):42-50.
International Search Report for PCT/US2019/067247, mailed Jun. 9, 2020.
Koeberl et al., "AAV Vector-mediated Reversal of Hypoglycemia in Canine and Murine Glycogen Storage Disease Type Ia," Molecular Therapy. (2008) vol. 16(4):665-672.
Lee et al., "The upstream enhancer elements of the G6PC promoter are critical for optimal G6PC expression in murine glycogen storage disease type Ia," Molecular Genetics and Metabolism. (2013) vol. 110:275-290.

(56)  References Cited

OTHER PUBLICATIONS

Lei et al., "Mutations in the glucose-6-phosphatase gene that cause glycogen disease type 1a," Science. (1993) vol. 262(5133):580-583.

Li et al., "Cellular immune response to cryptic epitopes during therapeutic gene transfer," Proceedings of the National Academy of Sciences. (2009) 106(26), 10770-10774.

Martin et al., "Generation and Characterization of Adeno-Associated Virus Producer Cell Lines for Research and Preclinical Vector Production," Human Gene Therapy Methods. (2013) vol. 24:253-269.

Nakai et al., "AAV serotype 2 vectors preferentially integrate into active genes in mice," Nat Genet. (2003) vol. 34(3):297-302.

Philpott et al., "Efficient Integration of Recombinant Adeno-Associated Virus DNA Vectors Requires a p5-rep Sequence in cis," Journal of Virology. (2002) vol. 76(11):5411-5421.

Rake et al., "Glycogen storage disease type I: diagnosis, management, clinical course and outcome. Results of the European Study on Glycogen Storage Disease Type I (ESGSD I)," Eur J Pediatr (2002) 161:S20-S34.

Samulski et al., "Helper-free stocks of recombinant adeno-associated viruses: normal integration does not require viral gene expression," Journal of Virology. (1989) vol. 63(9):3822-3828.

Sommer et al., "Quantification of adeno-associated virus particles and empty capsids by optical density measurement," (2003) 7(1):122-128.

Strobel et al., "Comparative Analysis of Cesium Chloride- and Iodixanol-Based Purification of Recombinant Adeno-Associated Viral Vectors for Preclinical Applications," Human Gene Therapy Methods. (2015) vol. 26(4):147-157.

Virag et al., "Producing Recombinant Adeno-Associated Virus in Foster Cells: Overcoming Production Limitations Using a Baculovirus-Insect Cell Expression Strategy", Human Gene Therapy. vol. 20, No. 8 (2009), pp. 807-817.

Thorne et al., "Manufacturing recombinant adeno-associated viral vectors from producer cell clones," Human Gene Therapy. (2009) vol. 20:707-714.

Wang et al., "Identification of an adeno-associated virus binding epitope for AVB sepharose affinity resin," Molecular Therapy—Methods and Clinical Development. (2015) vol. 2:1-6.

Wright, "Transient Transfection Methods for Clinical Adeno-Associated Viral Vector Production," Human Gene Therapy. (2009) vol. 20,:698-706.

Yuan et al., "A Versatile Adeno-Associated Virus Vector Producer Cell Line Method for Scalable Vector Production of Different Serotypes," Human Gene Therapy (2011) 22(5): 613-624.

Yiu et al., "Complete Normalization of Hepatic G6PC Deficiency in Murine Glycogen Storage Disease Type Ia Using Gene Therapy," Molecular Therapy. (2010) vol. 18(6), 1076-1084.

Zhen et al., "Infectious Titer Assay for Adeno-Associated Virus Vectors with Sensitivity Sufficient to Detect Single Infectious Events," Human Gene Therapy (2004) vol. 15(7):709-715.

Estécio et al. (2012) "SINE Retrotransposons Cause Epigenetic Reprogramming of Adjacent Gene Promoters," Mol Cancer Res. 10(10):1332-1342.

Powell et al. (2015) "Viral Expression Cassette Elements to Enhance Transgene Target Specificity and Expression in Gene Therapy," Discov Med. 19(102):49-57.

* cited by examiner

ABBREVIATIONS: GPE, G6Pase PROMOTER/ENHANCER REGION; hG6PCco, HUMAN GLUCOSE-6-PHOSPHATASE CODING REGION (CODON-OPTIMIZED); ITR, INVERTED TERMINAL REPEAT; SV40L pA, SV40 LATE POLYADENYLATION SIGNAL; UTR, UNTRANSLATED REGION

DTC161

WILD-TYPE
SIZE: 4768 bp

DTC175

Alu 1+2 DELETION
SIZE: 4238 bp

DTC176

Alu 1+2 REVERSAL
SIZE: 4768 bp

DTC177

Alu 1+2+3 DELETION
SIZE: 3882 bp

DTC178

Alu 3 DELETION
SIZE: 4412 bp

DTC179

Alu 3 REVERSAL
SIZE: 4768 bp

DTX.hG6PCco.401 (DTC161)
10,390 bp pDTX.hG6PC.401 FEATURES

| TYPE | START | END | DESCRIPTION |
|------|-------|-----|-------------|
| *REGION* | *1* | *145* | *INVERTED TERMINAL REPEAT (ITR)* |
| *REGION* | *146* | *3,009* | *G6PC PROMOTER/ENHANCER (GPE)* |
| *REGION* | *3,010* | *3,331* | *CHIMERIC INTRON* |
| *GENE* | *3,332* | *4,405* | *hG6PC CODON OPTIMIZED cDNA* |
| *REGION* | *4,426* | *4,623* | *SV40 LATE POLYADENYLATION SIGNAL* |
| *REGION* | *4,624* | *4,768* | *INVERTED TERMINAL REPEAT (ITR)* |

| | Reference Standard | DTC177 |
|---|---|---|
| YINTERCEPT | -6.87 | -6.93 |
| SLOPE | 1.34 | 1.34 |
| x-int | 5.14 | 5.14 |
| x-int[REF] – x-int[UNK] | | -0.048652695 |
| RELATIVE POTENCY | | 89% |

| | Reference Standard | DTC161 |
|---|---|---|
| YINTERCEPT | -5.49 | -5.61 |
| SLOPE | 1.22 | 1.22 |
| x-int | 4.52 | 4.62 |
| x-int[REF] – x-int[UNK] | | -0.099506579 |
| RELATIVE POTENCY | | 80% |

SEQUENCE LISTING

<160> NUMBER OF SEQ ID NOS: 15

<210> SEQ ID NO 1
<211> LENGTH: 3882
<212> TYPE: DNA
<213> ORGANISM: Artificial Sequence
<220> FEATURE:
<223> OTHER INFORMATION: Description of artificial sequence: DTC177: ITR
      to ITR

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctccttt gagaatccac ggtgtctcga tgcagtcagc     180
tttctaacaa gctggggcct cacctgtttt cccacggata aaaacgtgct ggaggaagca     240
gaaaggggct ggcaggtgga aagatgagga ccagctcatc gtctcatgac tatgaggttg     300
ctctgatcca gagggtcccc ctgcctggtg gcccaccgcc aggaagactc ccactgtccc     360
tggatgccca gagtgggatg tcaactccat cacttatcaa ctccttatcc ataggggtat     420
tcttcctgag gcgtctcaga aaacagggcc ctccccatat gctgaccaca taatagaacc     480
cctcccaact cagagaccct ggctgctagc tgccctggca tgacccagac agtggccttt     540
gtatatgttt ttagactcac cttgactcac ctctgaccat agaaactctc atcccagagg     600
tcactgcaat agttactcca caacagaggc ttatctgggt agagggaggc tccctaccta     660
```

-continued

```
tggcccagca gccctgacag tgcagatcac atataccca cgccccagca ctgcctgcca      720
cgcatgggct tactttacac ccacccacag tcaccaacac attacctgct ctccaaggtt      780
aggcgtggca ggagaagttt gcttggacca gcagaaacca tgcagtcaag gacaactgga      840
gtcagcatgg gctgggtgcg agcccttggt ggggtgggga ggagactcca ggtcatacct      900
cctggaggat gtttaatca tttccagcat ggaatgctgt caacttttgc cacagattca      960
ttagctctga gtttcttttt tctgtcccca gctacccctt acatgtcaat atggacttaa     1020
tgatgggaaa ttcaggcaag ttttaaaca ttttattccc cctggctctt atcctcaaaa     1080
aatgcatgag ttcgttacct gattcattcc ctggttcctt tcacagtcct ccgtgaccca     1140
agtgttaggg ttttggtctc tctactattt gtaggctgat atatagtata cacacacaca     1200
cacacacaca tatacacaca cacagtgtat cttgagcttt cttttgtata tctacacaca     1260
tatgtataag aaagctcaag atatagaagc ccttttttcaa aaataactga aagtttcaaa     1320
ctctttaagt ctccagttac cattttgctg gtattcttat ttggaaccat acattcatca     1380
tattgttgca cagtaagact atacattcat tattttgctt aaacgtatga gttaaaacac     1440
tttaaggtca ttaaatgaat taatcactgc attcaaaaac gattactttc tggccctaag     1500
agacatgagg ccaataccag gaaggggggtt gatctcccaa accagaggca gaccctagac     1560
tctaatacag ttaaggaaag accagcaaga tgatagtccc caatacaata gaactttact     1620
aattttaaaa ttaagaactt aaaacttgaa tagctagagc accaagattt ttctttgtcc     1680
ccaaataagt gcagttgcag gcatagaaaa tctgacatct ttgcaagaat catcgtggat     1740
gtagactctg tcctgtgtct ctggcctggt ttcggggacc aggagggcag acccttgcac     1800
tgccaagaag catgccaaag ttaatcattg gccctgctga gtacatggcc gatcaggctg     1860
tttttgtgtg cctgttttc tattttacgt aaatcaccct gaacatgttt gcatcaacct     1920
actggtgatg cacctttgat caatacattt tagacaaacg tggttttttga gtccaaagat     1980 cagggctggg ttgacctgaa tactggatac agggcatata aaacaggggc aaggcacaga     2040
ctcatagcag agcaatcacc accaagcctg gaataactgc aagggctctg ctgacatctt     2100
cctgaggtgc caaggaaatg aggtctagag aagctttatt gcggtagttt atcacagtta     2160
aattgctaac gcagtcagtg cttctgacac aacagtctcg aacttaagct gcagtgactc     2220
tcttaaggta gccttgcaga agttggtcgt gaggcactgg gcaggtaagt atcaaggtta     2280
caagacaggt ttaaggagac caatagaaac tgggcttgtc gagacagaga agactcttgc     2340
gtttctgata ggcacctatt ggtcttactg acatccactt tgcctttctc tccacaggtg     2400
tccactccca gttcaattac agctcttaag gccctgcagg ccaccatgga agagggcatg     2460
aacgtgctgc acgacttcgg catccagagc acccactatc tgcaggtcaa ctaccaggac     2520
agccaggact ggttcatcct ggtgtccgtg atcgccgacc tgcggaacgc cttctacgtg     2580
ctgttcccca tctggttcca tctgcaagaa gccgtcggca tcaagctgct gtgggtggcc     2640
gtgatcggcg attggctgaa cctggtgttc aagtggatcc tgttcggcca gcggccctat     2700
tggtgggtgc tggacaccga ctactacagc aacaccagcg tgcccctgat caagcagttc     2760
cccgtgacct gcgagacagg ccctggctct ccttctggcc acgccatggg aacagccggc     2820
gtgtactacg tgatggtcac cagcaccctg agcatcttcc agggcaagat caagcccacc     2880
taccggttcc ggtgcctgaa cgtgatcctg tggctgggct ctgggccgt gcagctgaac     2940 gtgtgcctga ccggatcta cctggccgcc cacttcccac atcaagtggt ggccggccgtg     3000 ctgagcggaa tcgccgtggc cgagacattc agccacatcc acagcatcta caacgccagc     3060
```

-continued

```
ctgaagaagt acttcctgat cacattcttt ctgttcagct tcgccatcgg cttctacctg      3120
ctgctgaagg gcctgggcgt ggacctgctg tggaccctgg aaaaggccca gcggtggtgc      3180
gagcagcccg agtgggtgca catcgacacc accccttcg ccagcctgct gaagaacctg       3240
ggcaccctgt ttggactggg cctggccctg aacagcagca tgtacagaga gagctgcaag      3300
ggcaagctga gcaagtggct gcccttccgg ctgagcagca tcgtggccag cctggtgctg      3360
ctgcacgtgt tcgacagcct gaagcccccc agccaggtgg aactggtgtt ttacgtgctg      3420
agcttctgca agagcgccgt ggtgcccctg gcctccgtgt ctgtgatccc ctactgcctg      3480
gctcaggtgc tgggccagcc ccacaagaag tccctctgag cgctctaggc ggccgcgcgg      3540
atccagacat gataagatac attgatgagt ttggacaaac cacaactaga atgcagtgaa      3600
aaaaatgctt tatttgtgaa atttgtgatg ctattgcttt atttgtaacc attataagct      3660
gcaataaaca agttaacaac aacaattgca ttcattttat gtttcaggtt cagggggagg      3720
tgtgggaggt tttttagagg aacccctagt gatggagttg gccactccct ctctgcgcgc      3780
tcgctcgctc actgaggccg cccgggcaaa gcccgggcgt cgggcgacct ttggtcgccc      3840
ggcctcagtg agcgagcgag cgcgcagaga gggagtggcc aa                        3882
```

```
<210> SEQ ID NO 2
<211> LENGTH: 3882
<212> TYPE: DNA
<213> ORGANISM: Artificial Sequence
<220> FEATURE:
<223> OTHER INFORMATION: Description of artificial sequence: DTC177wt:
      Replacement of coG6PC sequence with wildtype coding sequence

<400> SEQUENCE: 2
```

```
ttggccactc cctctctgcg cgctcgctcg ctcactgagg ccgggcgacc aaaggtcgcc         60
cgacgcccgg gctttgcccg ggcggcctca gtgagcgagc gagcgcgcag agagggagtg        120
gccaactcca tcactagggg ttcctccttt gagaatccac ggtgtctcga tgcagtcagc        180
tttctaacaa gctggggcct cacctgtttt cccacggata aaaacgtgct ggaggaagca        240
gaaaggggct ggcaggtgga aagatgagga ccagctcatc gtctcatgac tatgaggttg        300
ctctgatcca gagggtcccc ctgcctggtg gcccaccgcc aggaagactc ccactgtccc        360
tggatgccca gagtgggatg tcaactccat cacttatcaa ctccttatcc ataggggtat        420
tcttcctgag gcgtctcaga aaacagggcc ctccccatat gctgaccaca taatagaacc        480
cctcccaact cagagaccct ggctgctagc tgccctggca tgacccagac agtggccttt        540
gtatatgttt ttagactcac cttgactcac ctctgaccat agaaactctc atcccagagg        600
tcactgcaat agttactcca caacagaggc ttatctgggt agagggaggc tccctaccta        660
tggcccagca gccctgacag tgcagatcac atatacccca cgccccagca ctgcctgcca        720
cgcatgggct actttacac ccacccacag tcaccaacac attacctgct ctccaaggtt         780
aggcgtggca ggagaagttt gcttggacca gcagaaacca tgcagtcaag acaactgga         840 gtcagcatgg gctgggtgcg agcccttggt ggggtgggga ggagactcca ggtcatacct        900
cctggaggat gttttaatca tttccagcat ggaatgctgt caacttttgc cacagattca        960
ttagctctga gtttcttttt tctgtcccca gctacccctt acatgtcaat atggacttaa       1020
tgatgggaaa ttcaggcaag ttttttaaaca ttttattccc cctggctctt atcctcaaaa      1080
aatgcatgag ttcgttacct gattcattcc ctggttcctt tcacagtcct ccgtgaccca       1140
agtgttaggg ttttggtctc tctactattt gtaggctgat atatagtata cacacacaca      1200
```

-continued

```
cacacacaca tatacacaca cacagtgtat cttgagcttt cttttgtata tctacacaca      1260
tatgtataag aaagctcaag atatagaagc ccttttcaa aaataactga aagtttcaaa       1320
ctctttaagt ctccagttac cattttgctg gtattcttat ttggaaccat acattcatca     1380
tattgttgca cagtaagact atacattcat tattttgctt aaacgtatga gttaaaacac     1440
tttaaggtca ttaaatgaat taatcactgc attcaaaaac gattactttc tggccctaag     1500
agacatgagg ccaataccag gaaggggtt gatctcccaa accagaggca gaccctagac      1560
tctaatacag ttaaggaaag accagcaaga tgatagtccc caatacaata gaactttact     1620
aattttaaaa ttaagaactt aaaacttgaa tagctagagc accaagattt ttctttgtcc     1680
ccaaataagt gcagttgcag gcatagaaaa tctgacatct ttgcaagaat catcgtggat     1740
gtagactctg tcctgtgtct ctggcctggt ttcggggacc aggagggcag acccttgcac     1800
tgccaagaag catgccaaag ttaatcattg ccctgctga gtacatggcc gatcaggctg      1860
tttttgtgtg cctgttttc tattttacgt aaatcaccct gaacatgttt gcatcaacct      1920
actggtgatg cacctttgat caatacattt tagacaaacg tggttttga gtccaaagat      1980 cagggctggg ttgacctgaa tactggatac agggcatata aaacagggc aaggcacaga      2040 ctcatagcag agcaatcacc accaagcctg gaataactgc aagggctctg ctgacatctt     2100
cctgaggtgc caaggaaatg aggtctagag aagctttatt gcggtagttt atcacagtta     2160
aattgctaac gcagtcagtg cttctgacac aacagtctcg aacttaagct gcagtgactc     2220
tcttaaggta gccttgcaga agttggtcgt gaggcactgg gcaggtaagt atcaaggtta     2280
caagacaggt ttaaggagac caatagaaac tgggcttgtc gagacagaga agactcttgc     2340
gtttctgata ggcacctatt ggtcttactg acatccactt tgcctttctc tccacaggtg     2400
tccactccca gttcaattac agctcttaag gccctgcagg ccaccatgga ggaaggaatg     2460
aatgttctcc atgactttgg gatccagtca acacattacc tccaggtgaa ttaccaagac     2520
tcccaggact ggttcatctt ggtgtccgtg atcgcagacc tcaggaatgc cttctacgtc     2580
ctcttcccca tctggttcca tcttcaggaa gctgtgggca ttaaactcct ttgggtagct     2640
gtgattggag actggctcaa cctcgtcttt aagtggattc tctttggaca gcgtccatac     2700
tggtgggttt tggatactga ctactacagc aacacttccg tgccctgat aaagcagttc     2760 cctgtaacct gtgagactgg accagggagc ccctctggcc atgccatggg cacagcaggt     2820
gtatactacg tgatggtcac atctactctt tccatctttc agggaaagat aaagccgacc     2880
tacagatttc ggtgcttgaa tgtcattttg tggttgggat tctgggctgt gcagctgaat     2940
gtctgtctgt cacgaatcta ccttgctgct cattttcctc atcaagttgt tgctggagtc     3000
ctgtcaggca ttgctgttgc agaaactttc agccacatcc acagcatcta taatgccagc     3060
ctcaagaaat attttctcat taccttcttc ctgttcagct tcgccatcgg attttatctg     3120
ctgctcaagg gactgggtgt agacctcctg tggactctgg agaaagccca gaggtggtgc     3180
gagcagccag aatgggtcca cattgacacc acaccctttg ccagcctcct caagaacctg     3240
ggcacgctct ttggcctggg gctggctctc aactccagca gtacaggga gagctgcaag     3300 gggaaactca gcaagtggct cccattccgc ctcagctcta ttgtagcctc cctcgtcctc     3360
ctgcacgtct ttgactcctt gaaaccccca tcccaagtcg agctggtctt ctacgtcttg     3420
tccttctgca agagtgcggt agtgcccctg gcatccgtca gtgtcatccc ctactgcctc     3480
gcccaggtcc tgggccagcc gcacaagaag tcgttgtaag cgctctaggc ggccgcgcgg     3540
```

```
atccagacat gataagatac attgatgagt ttggacaaac cacaactaga atgcagtgaa    3600
aaaaatgctt tatttgtgaa atttgtgatg ctattgcttt atttgtaacc attataagct    3660
gcaataaaca agttaacaac aacaattgca ttcattttat gtttcaggtt caggggaggg    3720
tgtgggaggt tttttagagg aacccctagt gatggagttg gccactccct ctctgcgcgc    3780
tcgctcgctc actgaggccg cccgggcaaa gcccgggcgt cgggcgacct ttggtcgccc    3840
ggcctcagtg agcgagcgag cgcgcagaga gggagtggcc aa                       3882
```

```
<210> SEQ ID NO 3
<211> LENGTH: 1074
<212> TYPE: DNA
<213> ORGANISM: Artificial Sequence
<220> FEATURE:
<223> OTHER INFORMATION: Description of Artificial Sequence: Codon-
      optimized G6PC coding sequence

<400> SEQUENCE: 3
atggaagagg gcatgaacgt gctgcacgac ttcggcatcc agagcaccca ctatctgcag      60
gtcaactacc aggacagcca ggactggttc atcctggtgt ccgtgatcgc cgacctgcgg     120
aacgccttct acgtgctgtt ccccatctgg ttccatctgc aagaagccgt cggcatcaag     180
ctgctgtggg tggccgtgat cggcgattgg ctgaacctgg tgttcaagtg gatcctgttc     240
ggccagcggc cctattggtg ggtgctggac accgactact acagcaacac cagcgtgccc     300
ctgatcaagc agttccccgt gacctgcgag acaggccctg ctctccttc tggccacgcc      360 atgggaacag ccggcgtgta ctacgtgatg gtcaccagca ccctgagcat cttccagggc     420
aagatcaagc ccacctaccg gttccggtgc ctgaacgtga tcctgtggct gggcttctgg     480
gccgtgcagc tgaacgtgtg cctgagccgg atctacctgg ccgcccactt cccacatcaa     540
gtggtggccg gcgtgctgag cggaatcgcc gtggccgaga cattcagcca catccacagc     600
atctacaacg ccagcctgaa gaagtacttc ctgatcacat tctttctgtt cagcttcgcc     660
atcggcttct acctgctgct gaagggcctg ggcgtggacc tgctgtggac cctggaaaag     720
gcccagcggt ggtgcgagca gcccgagtgg gtgcacatcg acaccacccc cttcgccagc     780
ctgctgaaga acctgggcac cctgtttgga ctgggcctgg ccctgaacag cagcatgtac     840
agagagagct gcaagggcaa gctgagcaag tggctgccct ccggctgag cagcatcgtg      900 gccagcctgg tgctgctgca cgtgttcgac agcctgaagc cccccagcca ggtggaactg     960
gtgttttacg tgctgagctt ctgcaagagc gccgtggtgc ccctggcctc cgtgtctgtg    1020
atcccctact gcctggctca ggtgctgggc cagccccaca gaaagtccct ctga          1074
```

```
<210> SEQ ID NO 4
<211> LENGTH: 1074
<212> TYPE: DNA
<213> ORGANISM: Homo sapiens

<400> SEQUENCE: 4
atggaggaag gaatgaatgt tctccatgac tttgggatcc agtcaacaca ttacctccag       60
gtgaattacc aagactccca ggactggttc atcttggtgt ccgtgatcgc agacctcagg      120
aatgccttct acgtcctctt ccccatctgg ttccatcttc aggaagctgt gggcattaaa      180
ctcctttggg tagctgtgat tggagactgg ctcaacctcg tctttaagtg gattctcttt      240
ggacagcgtc catactggtg ggttttggat actgactact acagcaacac ttccgtgccc      300
ctgataaagc agttccctgt aacctgtgag actggaccag ggagcccctc tggccatgcc      360
```

```
atgggcacag caggtgtata ctacgtgatg gtcacatcta ctctttccat ctttcaggga     420
aagataaagc cgacctacag atttcggtgc ttgaatgtca ttttgtggtt gggattctgg     480
gctgtgcagc tgaatgtctg tctgtcacga atctaccttg ctgctcattt tcctcatcaa     540
gttgttgctg gagtcctgtc aggcattgct gttgcagaaa cttttcagcca catccacagc     600 atctataatg ccagcctcaa gaaatatttt ctcattacct tcttcctgtt cagcttcgcc     660
atcggatttt atctgctgct caagggactg ggtgtagacc tcctgtggac tctggagaaa     720
gcccagaggt ggtgcgagca gccagaatgg gtccacattg acaccacacc ctttgccagc     780
ctcctcaaga acctgggcac gctctttggc ctggggctgg ctctcaactc cagcatgtac     840
agggagagct gcaagggaa actcagcaag tggctcccat tccgcctcag ctctattgta     900
gcctccctcg tcctcctgca cgtctttgac tccttgaaac ccccatccca agtcgagctg     960
gtcttctacg tcttgtcctt ctgcaagagt gcggtagtgc ccctggcatc cgtcagtgtc    1020
atcccctact gcctcgccca ggtcctgggc cagccgcaca agaagtcgtt gtaa            1074
```

<210> SEQ ID NO 5
<211> LENGTH: 357
<212> TYPE: PRT
<213> ORGANISM: Homo sapiens

<400> SEQUENCE: 5

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255
```

```
Pro Phe Ala Ser Leu Leu Lys Asn Leu Gly Thr Leu Phe Gly Leu Gly
        260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
        290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
                340                 345                 350

His Lys Lys Ser Leu
        355

<210> SEQ ID NO 6
<211> LENGTH: 2864
<212> TYPE: DNA
<213> ORGANISM: Homo sapiens

<400> SEQUENCE: 6
cctttgagaa tccacggtgt ctcgatgcag tcagctttct aacaagctgg ggcctcacct     60
gttttcccac ggataaaaac gtgctggagg aagcagaaag gggctggcag gtggaaagat    120
gaggaccagc tcatcgtctc atgactatga ggttgctctg atccagaggg tccccctgcc    180
tggtggccca ccgccaggaa gactcccact gtccctggat gcccagagtg ggatgtcaac    240
tccatcactt atcaactcct tatccatagg ggtattcttc ctgaggcgtc tcagaaaaca    300
gggccctccc catatgctga ccacataata gaacccctcc caactcagag accctggctg    360
ctagctgccc tggcatgacc cagacagtgg cctttgtata tgtttttaga ctcaccttga    420
ctcacctctg accatagaaa ctctcatccc agaggtcact gcaatagtta ctccacaaca    480
gaggcttatc tgggtagagg gaggctccct acctatggcc cagcagccct gacagtgcag    540
atcacatata ccccacgccc cagcactgcc tgccacgcat gggcttactt tacacccacc    600
cacagtcacc aacacattac ctgctctcca aggttaggcg tggcaggaga agtttgcttg    660
gaccagcaga aaccatgcag tcaaggacaa ctggagtcag catgggctgg gtgcgagccc    720
ttggtggggt ggggaggaga ctccaggtca tacctcctgg aggatgtttt aatcatttcc    780
agcatggaat gctgtcaact tttgccacag attcattagc tctgagtttc ttttttctgt    840
ccccagctac cccttacatg tcaatatgga cttaatgatg ggaaattcag gcaagttttt    900
aaacatttta ttcccctgg ctcttatcct caaaaaatgc atgaatttgg aggcagtggc    960
tcatgcctgt aatcccaatg ctttgctagg ttgaggcggg aggatcactt gaagccagga   1020
atttgagacc agcctgggcc gcatagtgag accccgtttc tacaaaaata aataaataaa   1080
taataaataa tagtgatatg aagcatgatt aaatagccct attttttaaa atgcatgagt   1140
tcgttacctg attcattccc tggttccttt cacagtcctc cgtgacccaa gtgttagggt   1200
tttggtctct ctactatttg taggctgata tatagtatac acacacac acacacacat    1260 atacacacac acagtgtatc ttgagctttc ttttgtatat ctacacacat atgtataaga   1320
aagctcaaga tatagaagcc ctttttcaaa aataactgaa agtttcaaac tctttaagtc   1380
tccagttacc attttgctgg tattcttatt tggaaccata cattcatcat attgttgcac   1440
agtaagacta tacattcatt attttgctta aacgtatgag ttaaaacact tggccaggca   1500
```

```
tggtggttca cacctgtaat cccagagctt tgggaagcca agactggcag atctcttgag    1560
ctcaggaatt caagaccagc ctgggcaaca tggaaaaacc ccatctctac aaaagataga    1620
aaaattagcc aggcatggtg gcgtgtgcct gtggtcccag ctactcagga ggctgaggtg    1680
ggaggatcac attagcccag gaggttgagg ctgcagtgag ccgtgattat gccactgcac    1740
tccagcctgg gagacagagt gagaccctgt ttcaaaaaaa agagagagaa aatttaaaaa    1800
agaaaacaac accaagggct gtaactttaa ggtcattaaa tgaattaatc actgcattca    1860
aaaacgatta ctttctggcc ctaagagaca tgaggccaat accaggaagg gggttgatct    1920
cccaaaccag aggcagaccc tagactctaa tacagttaag gaaagaccag caagatgata    1980
gtccccaata caatagaagt tactatattt tatttgttgt ttttcttttg ttttgttttg    2040
ttttgttttg ttttgtttta gagactgggg tcttgctcga ttgcccaggc tgtagtgcag    2100
cggtgggaca atagctcact gcagactcca actcctgggc tcaagcaatc ctcctgcctc    2160
agcctcctga atagctggga ctacaagggg acaccatcac acacaccaaa acaatttttt    2220 aaattttgt gtagaaacga gggtcttgct ttgttgccca ggctggtctc caactcctgg    2280
cttcaaggga tcctcccacc tcagcctccc aaattgctgg gattacaggt gtgagccacc    2340
acaaccagcc agaactttac taattttaaa attaagaact taaaacttga atagctagag    2400
caccaagatt tttctttgtc cccaaataag tgcagttgca ggcatagaaa atctgacatc    2460
tttgcaagaa tcatcgtgga tgtagactct gtcctgtgtc tctggcctgg tttcggggac    2520
caggagggca gacccttgca ctgccaagaa gcatgccaaa gttaatcatt ggccctgctg    2580
agtacatggc cgatcaggct gttttttgtgt gcctgttttt ctattttacg taaatcaccc    2640
tgaacatgtt tgcatcaacc tactggtgat gcacctttga tcaatacatt ttagacaaac    2700 gtggttttttg agtccaaaga tcagggctgg gttgacctga atactggata cagggcatat    2760
aaaacagggg caaggcacag actcatagca gagcaatcac caccaagcct ggaataactg    2820
caagggctct gctgacatct tcctgaggtg ccaaggaaat gagg                     2864
```

<210> SEQ ID NO 7
<211> LENGTH: 2670
<212> TYPE: DNA
<213> ORGANISM: Artificial Sequence
<220> FEATURE:
<223> OTHER INFORMATION: Description of Artificial Sequence: wildtype
      GPE but lacking Alu - 1

<400> SEQUENCE: 7

```
cctttgagaa tccacggtgt ctcgatgcag tcagctttct aacaagctgg ggcctcacct      60
gttttcccac ggataaaaac gtgctggagg aagcagaaag gggctggcag gtggaaagat     120
gaggaccagc tcatcgtctc atgactatga ggttgctctg atccagaggg tcccctgcc      180 tggtggccca ccgccaggaa gactcccact gtccctggat gcccagagtg ggatgtcaac     240
tccatcactt atcaactcct tatccatagg ggtattcttc ctgaggcgtc tcagaaaaca     300
gggccctccc catatgctga ccacataata gaacccctcc caactcagag accctggctg     360
ctagctgccc tggcatgacc cagacagtgg cctttgtata tgtttttaga ctcaccttga     420
ctcacctctg accatagaaa ctctcatccc agaggtcact gcaatagtta ctccacaaca     480
gaggcttatc tgggtagagg gaggctccct acctatggcc cagcagccct gacagtgcag     540
atcacatata ccccacgccc cagcactgcc tgccacgcat gggcttactt tacacccacc     600
cacagtcacc aacacattac ctgctctcca aggttaggcg tggcaggaga agtttgcttg     660
```

-continued

```
gaccagcaga aaccatgcag tcaaggacaa ctggagtcag catgggctgg gtgcgagccc      720
ttggtggggt ggggaggaga ctccaggtca tacctcctgg aggatgtttt aatcatttcc      780
agcatggaat gctgtcaact tttgccacag attcattagc tctgagtttc tttttttctgt     840 ccccagctac cccttacatg tcaatatgga cttaatgatg ggaaattcag gcaagttttt      900
aaacatttta ttccccctgg ctcttatcct caaaaaatgc atgagttcgt tacctgattc      960
attccctggt tcctttcaca gtcctccgtg acccaagtgt tagggttttg gtctctctac      1020
tatttgtagg ctgatatata gtatacacac acacacacac acacatatac acacacacag      1080
tgtatcttga gctttctttt gtatatctac acacatatgt ataagaaagc tcaagatata      1140
gaagcccttt ttcaaaaata actgaaagtt tcaaactctt taagtctcca gttaccattt      1200
tgctggtatt cttatttgga accatacatt catcatattg ttgcacagta agactataca      1260
ttcattattt tgcttaaacg tatgagttaa aacacttggc caggcatggt ggttcacacc      1320
tgtaatccca gagctttggg aagccaagac tggcagatct cttgagctca ggaattcaag      1380
accagcctgg gcaacatgga aaaacccccat ctctacaaaa gatagaaaaa ttagccaggc     1440
atggtggcgt gtgcctgtgg tcccagctac tcaggaggct gaggtgggag gatcacatta      1500
gcccaggagg ttgaggctgc agtgagccgt gattatgcca ctgcactcca gcctgggaga      1560
cagagtgaga ccctgtttca aaaaaaagag agagaaaatt taaaaaagaa aacaacacca      1620
agggctgtaa ctttaaggtc attaaatgaa ttaatcactg cattcaaaaa cgattacttt      1680
ctggccctaa gagacatgag gccaatacca ggaaggggt tgatctccca aaccagaggc       1740
agaccctaga ctctaataca gttaaggaaa gaccagcaag atgatagtcc ccaatacaat      1800
agaagttact atattttatt tgttgttttt cttttgtttt gttttgtttt gttttgtttt      1860
gttttagaga ctggggtctt gctcgattgc ccaggctgta gtgcagcggt gggacaatag      1920
ctcactgcag actccaactc ctgggctcaa gcaatcctcc tgcctcagcc tcctgaatag      1980
ctgggactac aagggtacac catcacacac accaaaacaa tttttaaat ttttgtgtag       2040 aaacgagggt cttgctttgt tgcccaggct ggtctccaac tcctggcttc aagggatcct      2100
cccacctcag cctcccaaat tgctgggatt acaggtgtga gccaccacaa ccagccagaa      2160
ctttactaat tttaaaatta agaacttaaa acttgaatag ctagagcacc aagattttc       2220 tttgtcccca aataagtgca gttgcaggca tagaaatct gacatctttg caagaatcat       2280
cgtggatgta gactctgtcc tgtgtctctg gcctggtttc ggggaccagg agggcagacc      2340
cttgcactgc caagaagcat gccaaagtta atcattggcc ctgctgagta catggccgat      2400
caggctgttt ttgtgtgcct gttttttctat tttacgtaaa tcaccctgaa catgtttgca     2460
tcaacctact ggtgatgcac ctttgatcaa tacattttag acaaacgtgg tttttgagtc      2520
caaagatcag ggctgggttg acctgaatac tggatacagg gcatataaaa cagggggcaag     2580 gcacagactc atagcagagc aatcaccacc aagcctggaa taactgcaag ggctctgctg      2640
acatcttcct gaggtgccaa ggaaatgagg                                       2670
```

<210> SEQ ID NO 8
<211> LENGTH: 2528
<212> TYPE: DNA
<213> ORGANISM: Artificial Sequence
<220> FEATURE:
<223> OTHER INFORMATION: Description of Artificial Sequence: wildtype
      GPE but lacking Alu - 2

<400> SEQUENCE: 8

```
cctttgagaa tccacggtgt ctcgatgcag tcagctttct aacaagctgg ggcctcacct     60
gttttcccac ggataaaaac gtgctggagg aagcagaaag gggctggcag gtggaaagat    120
gaggaccagc tcatcgtctc atgactatga ggttgctctg atccagaggg tccccctgcc    180
tggtggccca ccgccaggaa gactcccact gtccctggat gcccagagtg ggatgtcaac    240
tccatcactt atcaactcct tatccatagg ggtattcttc ctgaggcgtc tcagaaaaca    300
gggccctccc catatgctga ccacataata gaacccctcc caactcagag accctggctg    360
ctagctgccc tggcatgacc cagacagtgg cctttgtata tgtttttaga ctcaccttga    420
ctcacctctg accatagaaa ctctcatccc agaggtcact gcaatagtta ctccacaaca    480
gaggcttatc tgggtagagg gaggctccct acctatggcc cagcagccct gacagtgcag    540
atcacatata ccccacgccc cagcactgcc tgccacgcat gggcttactt tacacccacc    600
cacagtcacc aacacattac ctgctctcca aggttaggcg tggcaggaga agtttgcttg    660
gaccagcaga aaccatgcag tcaaggacaa ctggagtcag catgggctgg gtgcgagccc    720
ttggtggggt ggggaggaga ctccaggtca tacctcctgg aggatgtttt aatcatttcc    780
agcatggaat gctgtcaact tttgccacag attcattagc tctgagtttc tttttttctgt    840 ccccagctac cccttacatg tcaatatgga cttaatgatg ggaaattcag gcaagttttt    900
aaacatttta ttcccctgg ctcttatcct caaaaaatgc atgaatttgg aggcagtggc    960
tcatgcctgt aatcccaatg ctttgctagg ttgaggcggg aggatcactt gaagccagga   1020
atttgagacc agcctgggcc gcatagtgag accccgtttc tacaaaaata aataaataaa   1080
taataaataa tagtgatatg aagcatgatt aaatagccct atttttttaaa atgcatgagt   1140 tcgttacctg attcattccc tggttccttt cacagtcctc cgtgacccaa gtgttagggt   1200
tttggtctct ctactatttg taggctgata tatagtatac acacacacac acacacacat   1260
atacacacac acagtgtatc ttgagctttc ttttgtatat ctacacacat atgtataaga   1320
aagctcaaga tatagaagcc cttttttcaaa aataactgaa agtttcaaac tctttaagtc   1380
tccagttacc attttgctgg tattcttatt tggaaccata cattcatcat attgttgcac   1440
agtaagacta tacattcatt attttgctta aacgtatgag ttaaaacact ttaaggtcat   1500
taaatgaatt aatcactgca ttcaaaaacg attactttct ggccctaaga gacatgaggc   1560
caataccagg aagggggttg atctcccaaa ccagaggcag accctagact ctaatacagt   1620
taaggaaaga ccagcaagat gatagtcccc aatacaatag aagttactat atttttatttg   1680 ttgtttttct tttgtttttgt tttgtttttgt tttgtttttgt tttagagact ggggtcttgc   1740
tcgattgccc aggctgtagt gcagcggtgg gacaatagct cactgcagac tccaactcct   1800
gggctcaagc aatcctcctg cctcagcctc ctgaatagct gggactacaa gggtacacca   1860
tcacacacac caaaacaatt tttttaaattt ttgtgtagaa acgagggtct tgctttgttg   1920
cccaggctgg tctccaactc ctggcttcaa gggatcctcc cacctcagcc tcccaaattg   1980
ctgggattac aggtgtgagc caccacaacc agccagaact ttactaattt taaaattaag   2040
aacttaaaac ttgaatagct agagcaccaa gattttttctt tgtccccaaa taagtgcagt   2100
tgcaggcata gaaaatctga catctttgca agaatcatcg tggatgtaga ctctgtcctg   2160
tgtctctggc ctggtttcgg ggaccaggag ggcagaccct tgcactgcca agaagcatgc   2220
caaagttaat cattggccct gctgagtaca tggccgatca ggctgttttt gtgtgcctgt   2280
ttttctattt tacgtaaatc accctgaaca tgtttgcatc aacctactgg tgatgcacct   2340
```

-continued

```
ttgatcaata cattttagac aaacgtggtt tttgagtcca aagatcaggg ctgggttgac    2400
ctgaatactg gatacagggc atataaaaca ggggcaaggc acagactcat agcagagcaa    2460
tcaccaccaa gcctggaata actgcaaggg ctctgctgac atcttcctga ggtgccaagg    2520
aaatgagg                                                             2528
```

<210> SEQ ID NO 9
<211> LENGTH: 2508
<212> TYPE: DNA
<213> ORGANISM: Artificial Sequence
<220> FEATURE:
<223> OTHER INFORMATION: Description of Artificial Sequence: wildtype
      GPE but lacking Alu - 3

<400> SEQUENCE: 9

```
cctttgagaa tccacggtgt ctcgatgcag tcagctttct aacaagctgg ggcctcacct      60
gttttcccac ggataaaaac gtgctggagg aagcagaaag gggctggcag gtggaaagat     120
gaggaccagc tcatcgtctc atgactatga ggttgctctg atccagaggg tcccctgcc     180 tggtggccca ccgccaggaa gactcccact gtccctggat gcccagagtg ggatgtcaac     240
tccatcactt atcaactcct tatccatagg ggtattcttc ctgaggcgtc tcagaaaaca     300
gggccctccc catatgctga ccacataata gaacccctcc caactcagag accctggctg     360
ctagctgccc tggcatgacc cagacagtgg cctttgtata tgtttttaga ctcaccttga     420
ctcacctctg accatagaaa ctctcatccc agaggtcact gcaatagtta ctccacaaca     480
gaggcttatc tgggtagagg gaggctccct acctatggcc cagcagccct gacagtgcag     540
atcacatata ccccacgccc cagcactgcc tgccacgcat gggcttactt tacacccacc     600
cacagtcacc aacacattac ctgctctcca aggttaggcg tggcaggaga gtttgcttg     660 gaccagcaga aaccatgcag tcaaggacaa ctggagtcag catgggctgg gtgcgagccc     720
ttggtggggt ggggaggaga ctccaggtca tacctcctgg aggatgtttt aatcatttcc     780
agcatggaat gctgtcaact tttgccacag attcattagc tctgagtttc ttttttctgt     840
ccccagctac cccttacatg tcaatatgga cttaatgatg ggaaattcag gcaagttttt     900
aaacatttta ttcccctgg ctcttatcct caaaaaatgc atgaatttgg aggcagtggc     960
tcatgcctgt aatcccaatg ctttgctagg ttgaggcggg aggatcactt gaagccagga    1020
atttgagacc agcctgggcc gcatagtgag accccgtttc tacaaaaata aataaataaa    1080
taataaataa tagtgatatg aagcatgatt aaatagccct atttttttaaa atgcatgagt    1140 tcgttacctg attcattccc tggttccttt cacagtcctc cgtgacccaa gtgttagggt    1200
tttggtctct ctactatttg taggctgata tatagtatac acacacacac acacacacat    1260
atacacacac acagtgtatc ttgagctttc ttttgtatat ctacacacat atgtataaga    1320
aagctcaaga tatagaagcc cttttcaaa aataactgaa agtttcaaac tctttaagtc    1380
tccagttacc attttgctgg tattcttatt tggaaccata cattcatcat attgttgcac    1440
agtaagacta tacattcatt attttgctta aacgtatgag ttaaaacact tggccaggca    1500
tggtggttca cacctgtaat cccagagctt tgggaagcca agactggcag atctcttgag    1560
ctcaggaatt caagaccagc ctgggcaaca tggaaaaacc ccatctctac aaaagataga    1620
aaaattagcc aggcatggtg gcgtgtgcct gtggtcccag ctactcagga ggctgaggtg    1680
ggaggatcac attagcccag gaggttgagg ctgcagtgag ccgtgattat gccactgcac    1740
tccagcctgg gagacagagt gagaccctgt ttcaaaaaaa agagagagaa aatttaaaaa    1800
```

-continued

```
agaaaacaac accaagggct gtaactttaa ggtcattaaa tgaattaatc actgcattca    1860
aaaacgatta ctttctggcc ctaagagaca tgaggccaat accaggaagg gggttgatct    1920
cccaaaccag aggcagaccc tagactctaa tacagttaag gaaagaccag caagatgata    1980
gtccccaata caatagaact ttactaattt taaaattaag aacttaaaac ttgaatagct    2040
agagcaccaa gatttttctt tgtccccaaa taagtgcagt tgcaggcata gaaaatctga    2100
catctttgca agaatcatcg tggatgtaga ctctgtcctg tgtctctggc ctggtttcgg    2160
ggaccaggag ggcagaccct tgcactgcca agaagcatgc caaagttaat cattggccct    2220
gctgagtaca tggccgatca ggctgttttt gtgtgcctgt ttttctattt tacgtaaatc    2280
accctgaaca tgtttgcatc aacctactgg tgatgcacct ttgatcaata cattttagac    2340
aaacgtggtt tttgagtcca aagatcaggg ctgggttgac ctgaatactg gatacagggc    2400
atataaaaca ggggcaaggc acagactcat agcagagcaa tcaccaccaa gcctggaata    2460
actgcaaggg ctctgctgac atcttcctga ggtgccaagg aaatgagg              2508
```

<210> SEQ ID NO 10
<211> LENGTH: 2334
<212> TYPE: DNA
<213> ORGANISM: Artificial Sequence
<220> FEATURE:
<223> OTHER INFORMATION: Description of Artificial Sequence: wildtype
    GPE, but lacking Alu - 1 and Alu - 2

<400> SEQUENCE: 10

```
cctttgagaa tccacggtgt ctcgatgcag tcagctttct aacaagctgg ggcctcacct      60
gttttcccac ggataaaaac gtgctggagg aagcagaaag gggctggcag gtggaaagat     120
gaggaccagc tcatcgtctc atgactatga ggttgctctg atccagaggg tcccctgcc      180 tggtggccca ccgccaggaa gactcccact gtccctggat gcccagagtg ggatgtcaac     240
tccatcactt atcaactcct tatccatagg ggtattcttc ctgaggcgtc tcagaaaaca     300
gggccctccc catatgctga ccacataata gaacccctcc caactcagag accctggctg     360
ctagctgccc tggcatgacc cagacagtgg cctttgtata tgtttttaga ctcaccttga     420
ctcacctctg accatagaaa ctctcatccc agaggtcact gcaatagtta ctccacaaca     480
gaggcttatc tgggtagagg gaggctccct acctatggcc cagcagccct gacagtgcag     540
atcacatata ccccacgccc cagcactgcc tgccacgcat gggcttactt tacacccacc     600
cacagtcacc aacacattac ctgctctcca aggttaggcg tggcaggaga agtttgcttg     660
gaccagcaga aaccatgcag tcaaggacaa ctggagtcag catgggctgg gtgcgagccc     720
ttggtggggt ggggaggaga ctccaggtca tacctcctgg aggatgtttt aatcatttcc     780
agcatggaat gctgtcaact tttgccacag attcattagc tctgagtttc ttttttctgt     840
ccccagctac cccttacatg tcaatatgga cttaatgatg ggaaattcag gcaagttttt     900
aaacatttta ttccccctgg ctcttatcct caaaaaatgc atgagttcgt tacctgattc     960
attccctggt tcctttcaca gtcctccgtg acccaagtgt tagggttttg gtctctctac    1020
tatttgtagg ctgatatata gtatacacac acacacac acacatatac acacacacag       1080
tgtatcttga gctttctttt gtatatctac acacatatgt ataagaaagc tcaagatata    1140
gaagcccttt ttcaaaaata actgaaagtt tcaaactctt taagtctcca gttaccattt    1200
tgctggtatt cttatttgga accatacatt catcatattg ttgcacagta agactataca    1260
ttcattattt tgcttaaacg tatgagttaa aacactttaa ggtcattaaa tgaattaatc    1320
```

```
actgcattca aaaacgatta ctttctggcc ctaagagaca tgaggccaat accaggaagg     1380
gggttgatct cccaaaccag aggcagaccc tagactctaa tacagttaag gaaagaccag     1440
caagatgata gtccccaata caatagaagt tactatattt tatttgttgt ttttcttttg     1500
ttttgttttg ttttgttttg ttttgtttta gagactgggg tcttgctcga ttgcccaggc     1560
tgtagtgcag cggtgggaca atagctcact gcagactcca actcctgggc tcaagcaatc     1620
ctcctgcctc agcctcctga atagctggga ctacaagggt acaccatcac acacaccaaa     1680
acaatttttt aaattttgt gtagaaacga gggtcttgct ttgttgccca ggctggtctc     1740
caactcctgg cttcaaggga tcctcccacc tcagcctccc aaattgctgg gattacaggt     1800
gtgagccacc acaaccagcc agaactttac taatttaaa attaagaact taaaacttga     1860
atagctagag caccaagatt tttctttgtc cccaaataag tgcagttgca ggcatagaaa     1920
atctgacatc tttgcaagaa tcatcgtgga tgtagactct gtcctgtgtc tctggcctgg     1980
tttcggggac caggagggca gacccttgca ctgccaagaa gcatgccaaa gttaatcatt     2040
ggccctgctg agtacatggc cgatcaggct gtttttgtgt gcctgttttt ctattttacg     2100
taaatcaccc tgaacatgtt tgcatcaacc tactggtgat gcacctttga tcaatacatt     2160
ttagacaaac gtggtttttg agtccaaaga tcagggctgg gttgacctga atactggata     2220
cagggcatat aaaacagggg caaggcacag actcatagca gagcaatcac caccaagcct     2280
ggaataactg caagggctct gctgacatct tcctgaggtg ccaaggaaat gagg          2334
```

<210> SEQ ID NO 11
<211> LENGTH: 2172
<212> TYPE: DNA
<213> ORGANISM: Artificial Sequence
<220> FEATURE:
<223> OTHER INFORMATION: Description of Artificial Sequence: wildtype
      GPE, but lacking Alu - 2 and Alu - 3

<400> SEQUENCE: 11

```
cctttgagaa tccacggtgt ctcgatgcag tcagctttct aacaagctgg ggcctcacct       60
gttttcccac ggataaaaac gtgctggagg aagcagaaag gggctggcag gtggaaagat      120
gaggaccagc tcatcgtctc atgactatga ggttgctctg atccagaggg tccccctgcc      180
tggtggccca ccgccaggaa gactcccact gtccctggat gcccagagtg ggatgtcaac      240
tccatcactt atcaactcct tatccatagg ggtattcttc ctgaggcgtc tcagaaaaca      300
gggccctccc catatgctga ccacataata gaacccctcc caactcagag accctggctg      360
ctagctgccc tggcatgacc cagacagtgg cctttgtata tgtttttaga ctcaccttga      420
ctcacctctg accatagaaa ctctcatccc agaggtcact gcaatagtta ctccacaaca      480
gaggcttatc tgggtagagg gaggctccct acctatggcc cagcagccct gacagtgcag      540
atcacatata ccccacgccc cagcactgcc tgccacgcat gggcttactt tacacccacc      600
cacagtcacc aacacattac ctgctctcca aggttaggcg tggcaggaga agtttgcttg      660
gaccagcaga aaccatgcag tcaaggacaa ctggagtcag catgggctgg gtgcgagccc      720
ttggtggggt ggggaggaga ctccaggtca tacctcctgg aggatgtttt aatcatttcc      780
agcatggaat gctgtcaact tttgccacag attcattagc tctgagtttc ttttttctgt      840
ccccagctac cccttacatg tcaatatgga cttaatgatg ggaaattcag gcaagttttt      900
aaacatttta ttcccctgg ctcttatcct caaaaaatgc atgaatttgg aggcagtggc      960
tcatgcctgt aatcccaatg ctttgctagg ttgaggcggg aggatcactt gaagccagga     1020
```

-continued

```
atttgagacc agcctgggcc gcatagtgag accccgtttc tacaaaaata aataaataaa    1080
taataaataa tagtgatatg aagcatgatt aaatagccct attttttaaa atgcatgagt    1140
tcgttacctg attcattccc tggttccttt cacagtcctc cgtgacccaa gtgttagggt    1200
tttggtctct ctactatttg taggctgata tatagtatac acacacacac acacacacat    1260
atacacacac acagtgtatc ttgagctttc ttttgtatat ctacacacat atgtataaga    1320
aagctcaaga tatagaagcc ctttttcaaa aataactgaa agtttcaaac tctttaagtc    1380
tccagttacc attttgctgg tattcttatt tggaaccata cattcatcat attgttgcac    1440
agtaagacta tacattcatt attttgctta aacgtatgag ttaaaacact ttaaggtcat    1500
taaatgaatt aatcactgca ttcaaaaacg attactttct ggccctaaga gacatgaggc    1560
caataccagg aagggggttg atctcccaaa ccagaggcag accctagact ctaatacagt    1620
taaggaaaga ccagcaagat gatagtcccc aatacaatag aactttacta attttaaaat    1680
taagaactta aaacttgaat agctagagca ccaagatttt tctttgtccc caaataagtg    1740
cagttgcagg catagaaaat ctgacatctt tgcaagaatc atcgtggatg tagactctgt    1800
cctgtgtctc tggcctggtt tcggggacca ggagggcaga cccttgcact gccaagaagc    1860
atgccaaagt taatcattgg ccctgctgag tacatggccg atcaggctgt ttttgtgtgc    1920
ctgtttttct attttacgta aatcaccctg aacatgtttg catcaaccta ctggtgatgc    1980
acctttgatc aatacatttt agacaaacgt ggttttgag tccaaagatc agggctgggg    2040
tgacctgaat actggataca gggcatataa aacaggggca aggcacagac tcatagcaga    2100
gcaatcacca ccaagcctgg aataactgca agggctctgc tgacatcttc ctgaggtgcc    2160
aaggaaatga gg                                                        2172
```

<210> SEQ ID NO 12
<211> LENGTH: 2314
<212> TYPE: DNA
<213> ORGANISM: Artificial Sequence
<220> FEATURE:
<223> OTHER INFORMATION: Description of Artificial Sequence: wildtype
      GPE, but lacking Alu - 1 and Alu - 3

<400> SEQUENCE: 12

```
cctttgagaa tccacggtgt ctcgatgcag tcagctttct aacaagctgg ggcctcacct      60
gttttcccac ggataaaaac gtgctggagg aagcagaaag gggctggcag gtggaaagat     120
gaggaccagc tcatcgtctc atgactatga ggttgctctg atccagaggg tcccctgcc     180 tggtggccca ccgccaggaa gactcccact gtccctggat gccagagtg ggatgtcaac     240 tccatcactt atcaactcct tatccatagg ggtattcttc ctgaggcgtc tcagaaaaca     300
gggccctccc catatgctga ccacataata gaacccctcc caactcagag accctggctg     360
ctagctgccc tggcatgacc cagacagtgg cctttgtata tgttttttaga ctcaccttga     420 ctcacctctg accatagaaa ctctcatccc agaggtcact gcaatagtta ctccacaaca     480
gaggcttatc tgggtagagg gaggctccct acctatggcc cagcagccct gacagtgcag     540
atcacatata ccccacgccc cagcactgcc tgccacgcat gggcttactt tacacccacc     600
cacagtcacc aacacattac ctgctctcca aggttaggcg tggcaggaga gtttgcttg     660 gaccagcaga aaccatgcag tcaaggacaa ctggagtcag catgggctgg gtgcgagccc     720
ttggtggggt ggggaggaga ctccaggtca tacctcctgg aggatgtttt aatcatttcc     780
agcatggaat gctgtcaact tttgccacag attcattagc tctgagtttc ttttttctgt     840
```

```
ccccagctac cccttacatg tcaatatgga cttaatgatg ggaaattcag gcaagttttt        900
aaacatttta ttccccctgg ctcttatcct caaaaaatgc atgagttcgt tacctgattc        960
attccctggt tcctttcaca gtcctccgtg acccaagtgt tagggttttg gtctctctac       1020
tatttgtagg ctgatatata gtatacacac acacacacac acacatatac acacacacag       1080
tgtatcttga gctttctttt gtatatctac acacatatgt ataagaaagc tcaagatata       1140
gaagcccttt ttcaaaaata actgaaagtt tcaaactctt taagtctcca gttaccattt       1200
tgctggtatt cttatttgga accatacatt catcatattg ttgcacagta agactataca       1260
ttcattattt tgcttaaacg tatgagttaa aacacttggc caggcatggt ggttcacacc       1320
tgtaatccca gagctttggg aagccaagac tggcagatct cttgagctca ggaattcaag       1380
accagcctgg gcaacatgga aaaaccccat ctctacaaaa gatagaaaaa ttagccaggc       1440
atggtggcgt gtgcctgtgg tcccagctac tcaggaggct gaggtgggag gatcacatta       1500
gcccaggagg ttgaggctgc agtgagccgt gattatgcca ctgcactcca gcctgggaga       1560
cagagtgaga ccctgtttca aaaaaagag agagaaaatt taaaaaagaa aacaacacca       1620
agggctgtaa ctttaaggtc attaaatgaa ttaatcactg cattcaaaaa cgattacttt       1680
ctggccctaa gagacatgag gccaatacca ggaagggggg tgatctccca aaccagaggc       1740
agaccctaga ctctaataca gttaaggaaa gaccagcaag atgatagtcc ccaatacaat       1800
agaactttac taattttaaa attaagaact taaaacttga atagctagag caccaagatt       1860
tttctttgtc cccaaataag tgcagttgca ggcatagaaa atctgacatc tttgcaagaa       1920
tcatcgtgga tgtagactct gtcctgtgtc tctggcctgg tttcggggac caggagggca       1980
gacccttgca ctgccaagaa gcatgccaaa gttaatcatt ggccctgctg agtacatggc       2040
cgatcaggct gtttttgtgt gcctgttttt ctattttacg taaatcaccc tgaacatgtt       2100
tgcatcaacc tactggtgat gcacctttga tcaatacatt ttagacaaac gtggtttttg       2160
agtccaaaga tcagggctgg gttgacctga atactggata cagggcatat aaaacagggg       2220
caaggcacag actcatagca gagcaatcac caccaagcct ggaataactg caagggctct       2280
gctgacatct tcctgaggtg ccaaggaaat gagg                                    2314
```

```
<210> SEQ ID NO 13
<211> LENGTH: 301
<212> TYPE: DNA
<213> ORGANISM: Artificial Sequence
<220> FEATURE:
<223> OTHER INFORMATION: Description of Artificial Sequence: Intron

<400> SEQUENCE: 13
agctttattg cggtagttta tcacagttaa attgctaacg cagtcagtgc ttctgacaca         60
acagtctcga acttaagctg cagtgactct cttaaggtag ccttgcagaa gttggtcgtg        120
aggcactggg caggtaagta tcaaggttac aagacaggtt taaggagacc aatagaaact        180
gggcttgtcg agacagagaa gactcttgcg tttctgatag gcacctattg gtcttactga        240
catccacttt gcctttctct ccacaggtgt ccactcccag ttcaattaca gctcttaagg        300
c                                                                          301
```

```
<210> SEQ ID NO 14
<211> LENGTH: 137
<212> TYPE: DNA
<213> ORGANISM: Artificial Sequence
<220> FEATURE:
<223> OTHER INFORMATION: Description of Artificial Sequence: SV40 polyA
```

-continued

```
        tail

<400> SEQUENCE: 14
ggccgctatt tgtgaaattt gtgatgctat tgctttattt gtaaccatta taagctgcaa      60
taaacaagtt aacaacaaca attgcattca ttttatgttt caggttcagg gggaggtgtg     120
ggaggttttt taggcat                                                    137

<210> SEQ ID NO 15
<211> LENGTH: 145
<212> TYPE: DNA
<213> ORGANISM: Artificial Sequence
<220> FEATURE:
<223> OTHER INFORMATION: Description of Artificial Sequence: AAV2 ITR

<400> SEQUENCE: 15
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                          145
```

METHODS AND COMPOSITIONS FOR TREATING GLYCOGEN STORAGE DISEASES

CROSS-REFERENCE TO RELATED APPLICATIONS

This application is a U.S. national stage application, filed under 35 U.S.C. § 371, of International Application No. PCT/US2019/067247, filed on Dec. 18, 2019, which claims the benefit of and priority to U.S. Provisional Application No. 62/781,380, filed on Dec. 18, 2018, the entire disclosure of each of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Dec. 16, 2019, is named DIM-010WO_SL_ST25.txt and is 42,290 bytes in size.

TECHNICAL FIELD OF THE INVENTION

This application relates generally to viral vectors, and more particularly adeno-associated viral vectors, for the treatment of glycogen storage diseases such as glycogen storage disease type Ia.

BACKGROUND OF THE INVENTION

Glycogen storage disease type Ia (also known as GSD-Ia or von Gierke disease) is an inherited disorder caused by the buildup of glycogen in the body's cells. The accumulation of glycogen in certain organs and tissues, especially the liver, kidneys, and small intestines, impairs their ability to function normally. GSD-Ia typically manifests during the first year of life with severe hypoglycemia and hepatomegaly caused by the accumulation of glycogen. Affected individuals exhibit growth retardation, delayed puberty, lactic acidemia, hyperlipidemia, hyperuricemia, and in adults a high incidence of hepatic adenomas. See Lei et al., 1993, *Science* 262:580-3.

GSD-Ia is a rare, orphan genetic disease caused by the deficiency of active glucose-6-phosphatase-alpha (G6Pase-α), a key enzyme involved in the maintenance of glucose homeostasis. G6Pase-α, encoded by the G6PC gene, catalyzes the hydrolysis of glucose-6-phosphate (G6P) to glucose and phosphate in the final step of glycogenolysis and gluconeogenesis. Over 80 mutations responsible for G6Pase-α deficiency and the associated development of GSD-Ia have been identified to date. See Chou et al., 2010, *Nat Rev Endocrinol* 6 (12): 676-88.

There is presently no cure for GSD-Ia and dietary supplementation is the current standard of care for patients. When followed strictly, dietary strategies typically allow for normal growth and puberty development, however dietary therapy fails to completely prevent the occurrence of hyperlipidemia, hyperuricemia, lactic acidemia, and accumulation of liver fat. See Rake et al., 2002, *Eur J Pediatr* 161 Suppl 1: S20-34.

Gene therapy approaches using recombinant adeno-associated viruses (AAV) carrying G6Pase-α have been explored for the management of GSD-Ia. See, e.g., U.S. Pat. No. 9,644,216 and US Patent Publication No. 2017/0362670. However, to use AAV vectors for human gene therapy, the development of robust, reliable, and scalable production processes for the vectors is crucial. The present inventors have discovered that modifying the promoter/enhancer region of the G6PC gene to remove certain sequences, described herein as "Alu elements," dramatically improves rAAV yield and quality when expressed from various host cell platforms.

SUMMARY OF THE INVENTION

This invention provides methods and compositions for treating glycogen storage diseases. More specifically, provided herein are recombinant nucleic acid molecules, adeno-associated virus (AAV) vectors, and recombinant adeno-associated virus (rAAV) that can be used in gene therapy applications for the treatment of GSD-Ia.

In one aspect, the application relates to a recombinant nucleic acid molecule comprising a modified G6PC promoter/enhancer (GPE) sequence, wherein the modified GPE lacks one or more sequences at least 80% identical to an Alu element. In some embodiments, the Alu element is selected from the contiguous nucleotides 934-1127 (Alu-1), 1488-1823 (Alu-2), and 1995-2350 (Alu-3) of SEQ ID NO: 6. In some embodiments, the modified GPE has a sequence 80% (e.g., 80%, 85%, 90%, 95%, or 100%) identical to the contiguous nucleotides 146-2123 of SEQ ID NO: 1, or 80% (e.g., 80%, 85%, 90%, 95%, or 100%) identical to any one of SEQ ID NO: 7, 8, 9, 10, 11, or 12.

In another aspect, the application relates to a recombinant nucleic acid molecule comprising a modified G6PC promoter/enhancer (GPE) sequence described herein and a G6Pase-α coding sequence, wherein the modified GPE is capable of directing the expression of the G6Pase-α coding sequence. In some embodiments, the G6Pase-α coding sequence comprises a sequence at least 80% (e.g., 80%, 85%, 90%, 95%, or 100%) identical to SEQ ID NO: 3 or SEQ ID NO: 4. In some embodiments, the recombinant nucleic acid molecule further comprises a polyadenylation (polyA) signal sequence, such as an SV40 polyA signal sequence (SEQ ID NO: 14). In some embodiments, the recombinant nucleic acid molecule further comprises an intron (SEQ ID NO: 13). In some embodiments, the recombinant nucleic acid molecule comprises SEQ ID NO: 1 or SEQ ID NO: 2.

In another aspect, the application relates to a recombinant vector comprising a recombinant nucleic acid molecule described herein. In some embodiments, the vector is an adeno-associated virus (AAV) vector, such as an AAV vector of serotype 1, 2, 3, 4, 5, 6, 7, 8, 9, 10, 11, 12, or rh10 (i.e., AAV1, AAV2, AAV3, AAV4, AAV5, AAV6, AAV7, AAV8, AAV9, AAV10, AAV11, AAV12, or rh10). In an exemplary embodiment, the AAV vector is an AAV serotype 8 (AAV8) vector. Further provided are host cells comprising a recombinant nucleic acid molecule or a recombinant vector disclosed herein. In specific embodiments, the host cells may be suitable for the propagation of AAV.

In another aspect, the application relates to a method of increasing rAAV yield, and the method comprises delivering an AAV vector described herein to a host cell culture and harvesting the rAAV from the cell culture. In some embodiments, the host cell culture is a eukaryotic host cell culture.

Also provided herein is an rAAV comprising a recombinant nucleic acid molecule or an AAV vector disclosed herein. In some embodiments, the application relates to an rAAV for the treatment of GSD-Ia, and the an rAAV comprising an AAV capsid, and an AAV vector genome packaged therein, said AAV vector genome comprises an AAV 5' inverted terminal repeat sequence (ITR) sequence; a modified GPE sequence disclosed herein; a coding sequence encoding a glucose-6-phosphatase alpha (G6Pase-α), or an active fragment or variant thereof; and an AAV 3' ITR sequence. In some exemplary embodiments, the AAV capsid is an AAV8 capsid. In some embodiments, the vector genome includes the 5' and 3' ITR sequence identical to SEQ ID NO: 15. In some embodiments, the vector genome includes the modified GPE which comprises the contiguous nucleotides 146-2123 of SEQ ID NO: 1. In some embodiments, the vector genome further comprises a polyadenylation (polyA) signal sequence, e.g., an SV40 polyA signal sequence (SEQ ID NO: 14). In some embodiments, the vector genome further comprises an intron (SEQ ID NO: 13). In some embodiments, G6Pase-α comprises an amino acid sequence at least 80% (e.g., 80%, 85%, 90%, 95%, or 100%) identical to SEQ ID NO: 5. In some embodiments, the amino acid sequence of G6Pase-α comprises SEQ ID NO: 5. In some embodiments, the amino acid sequence of G6Pase-α consists of SEQ ID NO: 5. In some embodiments, the coding sequence of G6Pase-α is at least 80% (e.g., 80%, 85%, 90%, 95%, or 100%) identical to SEQ ID NO: 3 or SEQ ID NO: 4. In some exemplary embodiments, the vector genome comprises a nucleic acid sequence identical to SEQ ID NO: 1 or 2.

The application further relates to pharmaceutical compositions comprising an rAAV of the invention. In some embodiments, the pharmaceutical composition comprises a pharmaceutically acceptable carrier or excipient. In some embodiments, the pharmaceutical composition is formulated for subcutaneous, intramuscular, intradermal, intraperitoneal, or intravenous administration. In an exemplary embodiment, the pharmaceutical composition is formulated for intravenous administration.

In yet another aspect, the application relates to methods of treating glycogen storage disease type Ia (GSD-Ia) in a human subject comprising administering to the human subject a therapeutically effective amount of an rAAV disclosed herein. In some embodiments, the rAAV is administered subcutaneously, intramuscularly, intradermally, intraperitoneally, or intravenously. In an exemplary embodiment, the rAAV is administered intravenously. In some embodiments, the rAAV is administered at a dose of about $1 \times 10^{11}$ to about $1 \times 10^{14}$ genome copies (GC)/kg. In further embodiments, the rAAV is administered at a dose of about $1 \times 10^{12}$ to about $1 \times 10^{13}$ genome copies (GC)/kg. In some embodiments, a single dose of rAAV is administered. In other embodiments, multiple doses of rAAV are administered.

These and other aspects and features of the invention are described in the following sections of the application.

BRIEF DESCRIPTION OF THE DRAWINGS

The invention can be more completely understood with reference to the following drawings.

DETAILED DESCRIPTION OF THE INVENTION

Figures 1A, 1B:
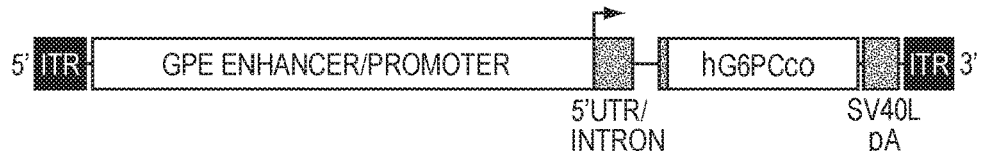
FIG. 1A is a schematic representation of the G6PC expression cassette bounded by two AAV2 inverted terminal repeats (ITRs, SEQ ID NO: 15) and comprising a GPE, an intron, a codon-optimized human G6PC gene (hG6PCco), and an SV40 late poly A tail.
FIG. 1B is an illustration of G6PC expression cassettes containing the wild-type (DTC161) or modified GPE (DTC175 comprising a G6PC expression cassette comprising a GPE with a deletion of the Alu-1 and Alu-2 sequences, DTC176 comprising a G6PC expression cassette comprising a GPE in which all three Alu elements are present but the orientations of the Alu 1 and Alu-2 sequences are reversed, DTC177 comprising a G6PC expression cassette comprising a GPE with a deletion of the Alu-1, Alu-2 and Alu-3 sequences, DTC178 comprising a G6PC expression cassette comprising a GPE with a deletion of the Alu-3 sequence, and DTC179 comprising a G6PC expression cassette comprising a GPE in which all three Alu elements are present but the orientation of the Alu-3 sequence is reversed).

This invention provides a range of novel agents and compositions to be used for therapeutic applications. The molecules and compositions of this invention can be used for ameliorating, preventing or treating disease associated with glycogen storage disease type Ia (GSD-Ia) or increasing the presence or function of glucose-6-phosphatase-alpha (G6Pase-α) in a subject.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 12 recognized serotypes of AAV (AAV1-12).

Administration/Administer: To provide or give a subject an agent, such as a therapeutic agent (e.g., a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

G6PC: A gene located on human chromosome 17q21 that encodes glucose-6-phosphatase-α (G6Pase-α). G6Pase-α is a 357 amino acid hydrophobic protein having 9 helices that anchor it in the endoplasmic reticulum (Chou et al., *Nat Rev Endocrinol* 6:676-688, 2010). The G6Pase-α protein catalyzes the hydrolysis of glucose 6-phosphate to glucose and phosphate in the terminal step of gluconeogenesis and glycogenolysis and is a key enzyme in glucose homeostasis. Mutations in the G6PC gene cause glycogen storage disease type Ia (GSD-Ia), which is a metabolic disorder characterized by severe fasting hypoglycemia associated with the accumulation of glycogen and fat in the liver and kidneys.

Glycogen storage disease (GSD): A group of diseases that result from defects in the processing of glycogen synthesis or breakdown within muscles, liver and other tissues. GSD can either be genetic or acquired. Genetic GSD is caused by any inborn error of metabolism involved in these processes. There are currently 11 recognized glycogen storage diseases (GSD type I, II, III, IV, V, VI, VII, IX, XI, XII and XIII). GSD-I consists of two autosomal recessive disorders, GSD-Ia and GSD-Ib (Chou et al., *Nat Rev Endocrinol* 6:676-688, 2010). GSD-Ia results from a deficiency in glucose-6-phosphatase-α. Deficiencies in the glucose-6-phosphate transporter (G6PT) are responsible for GSD-Ib.

Glycogen storage disease type Ia (GSD-Ia): Also known as von Gierke disease, GSD-Ia is the most common glycogen storage disease, having an incidence of about 1 in 100,000 live births. GSD-Ia is a genetic disease resulting from deficiency of the enzyme glucose-6-phosphatase-α (G6Pase-α). Deficiency in G6Pase-α impairs the ability of the liver to produce free glucose from glycogen and from gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia (Chou et al., *Nat Rev Endocrinol* 6:676-688, 2010). There is currently no cure for GSD-Ia.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are required for vector encapsidation.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as GSD-Ia) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g., a gene). A promoter includes necessary nucleic acid sequences near the start site of transcription.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule such as a recombinant nucleic acid molecule encoding G6Pase-α) has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; *Needleman & Wunsch, J. Mol. Biol.* 48:443, 1970: Pearson & Lipman, *Proc. Natl. Acad. Sci. USA* 85:2444, 1988; Higgins & Sharp, *Gene,* 73:237-44, 1988; Higgins & Sharp, *CABIOS* 5: 151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Rio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Therapeutically effective amount: A quantity of a specified pharmaceutical or therapeutic agent (e.g., a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

I. A Recombinant Nucleic Acid

One aspect of the invention provides a recombinant nucleic acid sequence, which includes a modified G6PC promoter/enhancer (GPE) lacking one or more Alu elements compared to the wild-type GPE, wherein the modified GPE is capable of directing the expression of a coding sequence encoding G6Pase-α (SEQ ID NO: 5). In some embodiments, the modified GPE is obtained by removing one or more Alu elements from the endogenous promoter for human G6PC gene, such as removing one or more of the contiguous nucleotides 934-1127 (Alu-1), 1488-1823 (Alu-2), and 1995-2350 (Alu-3) of SEQ ID NO: 6. In some other embodiments, the modified GPE is obtained by removing one or more Alu elements from the endogenous promoter for the G6PC gene of other mammals, such as non-human primates, sheep, rodents etc. In some embodiments, the modified GPE does not affect the G6PC gene expression in comparison with the wild-type GPE. In some embodiments, the modified GPE is capable of enhancing the expression of G6PC gene in comparison with the wild-type GPE. In some embodiments, the modified GPE has comparable activity to drive G6PC gene expression in the liver as the wild-type GPE, and very low activity to drive G6Pase-α expression in other tissues.

In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to the contiguous nucleotides 934-1127 (Alu-1) from SEQ ID NO: 6. In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to the contiguous nucleotides 1488-1823 (Alu-2) from SEQ ID NO: 6. In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to the contiguous nucleotides 1995-2350 (Alu-3) from SEQ ID NO: 6.

In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-1 and a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-2 from SEQ ID NO: 6. In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-1 and a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-3 from SEQ ID NO: 6. In some embodiments, the modified GPE includes a nucleic acid sequence devoid of a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-2 and a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-3 from SEQ ID NO: 6. In some embodiments, the modified GPE includes a nucleic acid sequence devoid of a sequence at least 80%

(e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-1, a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-2, and a sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to Alu-3 from SEQ ID NO: 6.

In some embodiments of the current invention, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to the contiguous nucleotides 146-2123 of SEQ ID NO: 1, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 7, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 8, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 9, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 10, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 11, wherein the GPE is capable of directing the expression of a coding sequence encoding G6Pase-α. In some embodiments, the recombinant nucleic acid sequence includes a GPE with a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 12, wherein the GPE is capable of directing the expression of a coding sequence encoding G6Pase-α.

Another aspect of the invention provides a recombinant nucleic acid sequence that includes a modified GPE disclosed herein and a coding sequence encoding G6Pase-α. In some embodiments, the G6Pase-α includes an amino acid sequence that is at least 80%, at least 85%, at least 90%, at least 95%, at least 96%, at least 97%, at least 98%, or at least 99% identical to SEQ ID NO: 5. In some embodiments, the G6Pase-α includes SEQ ID NO: 5 or an active fragment or variant thereof. In an exemplary embodiment, the G6Pase-α comprises or consists of SEQ ID NO: 5.

In some embodiments, the coding sequence encoding G6Pase-α incorporates a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 4.

In some embodiments, the coding sequence encoding human G6Pase-α is codon optimized for expression in human cells. Codon optimization can be performed on human G6PC cDNA using OptimumGene™ codon optimization technology (GenScript, Piscataway, NJ). The optimized G6PC cDNA sequences may be examined and further modified to eliminate potential alternative reading frames (ARFs) from internal non-in-frame ATG sequences that could theoretically encode peptides of 9 or more amino acids in length. For example, further modification can be performed on the codon-optimize G6PC cDNA sequences to avoid potential cytotoxic T lymphocyte responses to transgene products generated from ARFs (Li et al., 2009, *PNAS* 106:10770-4). In some embodiments, the codon-optimized encoding sequence for human G6Pase-α incorporates a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 3.

In some embodiments, the recombinant nucleic acid sequence that includes the modified GPE and the coding sequence encoding G6Pase-α as described herein further includes an intron and/or a polyadenylation signal. In some embodiments, the intron is placed between the GPE and the G6Pase-α coding sequence. In some embodiments, the intron is a chimeric intron, which increases the G6Pase-α transgene expression. The intron can be composed of the 5'-donor site from the first intron of the human β-globin gene and the branch and 3'-acceptor site from the intron of an immunoglobulin gene heavy chain variable region, wherein the sequences of the donor and acceptor sites, along with the branchpoint site, have been changed to match the consensus sequences for splicing. In some embodiments, the intron includes a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 13.

A polyadenylation signal can be placed downstream of the coding sequence encoding G6Pase-α for efficient polyadenylation of the G6PC mRNA. A variety of polyadenylation signals can be used, for example, a Simian virus 40 (SV40) late polyadenylation signal, an hGH polyadenylation signal, a BGH polyadenylation signal, or an rbGlob polyadenylation signal. In some embodiments, the polyadenylation signal is an SV40 late polyadenylation signal. In some embodiments, the polyadenylation signal includes has a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 14.

Another aspect of the invention provides a recombinant vector that includes a modified GPE, and a coding sequence encoding G6Pase-α disclosed herein. In some embodiments, the recombinant vector further includes an intron and/or a polyadenylation signal described herein. The vector can be a mammalian expression vector, a bacterial expression vector, a yeast expression vector, a lentivirus vector, a retrovirus vector, an adenovirus vector, an adeno-associated virus (AAV) vector, a RNAi vector, a Cre-Lox expression vector, a CRISPR expression vector, a TALEN expression vector, etc. The vector can further include an intron and/or a polyadenylation signal as described herein. In some embodiments, the recombinant vector further includes a stuffer nucleic acid sequence situated between the GPE and the intron, and/or between the intron and the G6Pase-α coding sequence.

In some embodiments, the recombinant vector is an AAV vector. The AAV vector can be an AAV vector of serotype 1, 2, 3, 4, 5, 6, 7, 8, 9, 10, 11, or 12 (i.e., AAV1, AAV2, AAV3, AAV4, AAV5, AAV6, AAV7, AAV8, AAV9, AAV10, AAV11, or AAV12), as well as any one of the more than 100 variants isolated from human and nonhuman primate tissues (See, e.g., Choi et al., Curr Gene Ther., 5:299-310, 2005; and Gao et al., Curr Gene Ther., 5:285-297, 2005). AAV vectors of any serotype may be used in the present invention, and the selection of AAV serotype will depend in part on the cell type(s) that are targeted for gene therapy. For treatment of GSD-Ia, liver is one of the relevant target organs.

In some embodiments, the recombinant AAV vector includes an AAV ITR sequence, which functions as both the origin of vector DNA replication and the packaging signal of the vector genome, when AAV and adenovirus helper functions are provided in trans. Additionally, the ITRs serve as the target for single-stranded endonucleatic nicking by the large Rep proteins, resolving individual genomes from replication intermediates.

In some exemplary embodiments, the AAV vector is an AAV serotype 8 (AAV8) vector, and the vector includes a modified GPE, an intron, a coding sequence encoding G6Pase-α, and an SV40 late polyadenylation signal described herein. In some embodiments, the vector further includes two AAV2 inverted terminal repeat (ITR) sequences (SEQ ID NO: 15): one 5' of the GPE and one 3' of the polyadenylation signal. In some particular non-limiting examples, the recombinant vector includes a nucleic acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO: 1 or SEQ ID NO: 2.

II. A Host Cell Comprising a Recombinant Nucleic Acid

Further provided are isolated host cells comprising the recombinant nucleic acid molecules or vectors disclosed herein. A vast range of host cells can be used, such as bacteria, yeast, insect, mammalian cells, etc. In some embodiments, the host cell can be a cell (or a cell line) appropriate for production of recombinant AAV (rAAV), for example, a HeLa, Cos-7, HEK293, A549, BHK, Vero, RD, HT-1080, ARPE-19, or MRC-5 cell.

The recombinant nucleic acid molecules or vectors can be delivered into the host cell culture using any suitable method known in the art. In some embodiments, a stable host cell line that has the recombinant nucleic acid molecule or vector inserted into its genome is generated. In some embodiments, a stable host cell line is generated, which contains an AAV vector described herein. After transfection of the AAV vector to the host culture, integration of the rAAV into the host genome can be assayed by various methods, such as antibiotic selection, fluorescence-activated cell sorting, southern blot, PCR based detection, fluorescence in situ hybridization as described by Nakai et al., Nature Genetics (2003) 34, 297-302; Philpott et al., Journal of Virology (2002) 76 (11): 5411-5421, and Howden et al., J Gene Med 2008; 10:42-50. Furthermore, a stable cell line can be established according to protocols well known in the art, such as those described in Clark, Kidney International Vol 61 (2002): S9-S15, and Yuan et al., Human Gene Therapy 2011 May; 22 (5): 613-24.

III. A Recombinant AAV

This invention also provides an rAAV comprising an AAV capsid and an AAV vector genome described herein. The AAV capsid can be serotype 1, 2, 3, 4, 5, 6, 7, 8, 9, 10, 11 or 12 (i.e., AAV1, AAV2, AAV3, AAV4, AAV5, AAV6, AAV7, AAV8, AAV9, AAV10, AAV11, AAV12, or rh10). In some embodiments, the capsid is an AAV8 capsid.

An rAAV can be produced by host cells, which are supplied with the AAV vectors disclosed herein and AAV Rep and Cap gene functions, as well as additional helper functions. The Rep and Cap gene functions can be provided to the host cell by various means, for example, by a plasmid or any type of vector containing the wild-type AAV Rep and Cap genes, and electroporation of Rep and Cap mRNAs. Additional helper functions can be provided by, for example, an adenovirus (AV) infection, by a plasmid that carries all of the required AV helper function genes, or by other viruses such as herpes simplex virus (HSV) or baculovirus. Any genes, gene functions, or other genetic material necessary for rAAV production by the host cell may transiently exist within the host cell, or be stably inserted into the host cell genome. rAAV production methods suitable for use with the methods of the current invention include those disclosed in Clark et al., Human Gene Therapy 6:1329-1341 (1995), Martin et al., Human Gene Therapy Methods 24:253-269 (2013), Thorne et al., Human Gene Therapy 20:707-714 (2009), Fraser Wright, Human Gene Therapy 20:698-706 (2009), and Virag et al., Human Gene Therapy 20:807-817 (2009).

In an exemplary embodiment, HEK293 cells are transfected with the AAV vector that includes the nucleic acid sequence of SEQ ID NO: 1 or SEQ ID NO: 2; a plasmid that encodes four wild-type AAV2 viral replication (Rep) proteins and the three wild-type AAV viral capsid (cap) proteins from serotype 8; and a plasmid containing regions of an adenovirus genome that are important for AAV replication, namely E2A, E4 and VA RNA. The rAAVs containing an AAV8 capsid can be subsequently produced and isolated from the host cells. In some embodiments, the modified GPE lacking one or more of the Alu elements in the AAV vector enhances packaging of the rAAV produced from the host cells. In some embodiments, the modified GPE lacking one or more of the Alu elements in the AAV vector affects self-complementary structure formation and hence enhances the yield of the rAAV produced from the host cells.

Lysis of AAV-infected cells can be accomplished by methods that chemically or enzymatically treat the cells in order to release infectious viral particles. These methods include the use of nucleases such as benzonase or DNAse, proteases such as trypsin, or detergents or surfactants. Physical disruption, such as homogenization or grinding, or the application of pressure via a microfluidizer pressure cell, or freeze-thaw cycles may also be used. Alternatively, supernatant may be collected from AAV-infected cells without the need for cell lysis.

It may be necessary to purify the sample containing rAAV and helper virus particles to remove, for example, the cellular debris resulting from cell lysis. Methods of minimal purification of helper virus and AAV particles are known in the art, and any appropriate method can be used to prepare samples containing both AAV and helper virus particles for use in the methods of the present invention. Two exemplary purification methods are cesium chloride (CsCl)- and iodixanol-based density gradient purification. Both methods are described in Strobel et al., Human Gene Therapy Methods, 26 (4): 147-157 (2015). Minimal purification can also be accomplished using affinity chromatography using, for example AVB Sepharose affinity resin (GE Healthcare Bio-Sciences AB, Uppsala, Sweden) or a POROS™ CaptureSelect™ AAV8, AAV9, or AAVX affinity resin (Thermo Fisher Scientific, Millersburg, PA). Methods of AAV purification using AVB Sepharose affinity resin are described in, for example, Wang et al., Mol Ther Methods Clin Dev., 2:15040 (2015).

It may be necessary to inactivate helper virus by heat. Heat inactivation techniques are based on the different thermal stabilities of AAV and helper virus particles. For example, AAV particles can be heated to temperatures as high as 56° C. and still remain intact, while AV particles are rendered inactive. Conway et al., Gene Therapy 6, 986-993, 1999, describes differential heat inactivation of HSV in AAV containing samples. Heat inactivation may be accomplished by any known methodology. In the examples described below, heat inactivation was accomplished using a thermocycler to rapidly heat and cool sample volumes of 300 μL or less. This system was chosen because it relies on heat transfer that is primarily conductive, making it a viable model for both continuous-flow systems and for larger batch systems that employ active mixing. Examples of continuous-flow systems include passage of the sample through a continuous-flow heat exchanger, such as the DHX™ Single-Use Heat Exchanger for Bio-therapeutic Manufacturing (Thermo Fisher Scientific, Millersburg, PA). Such systems allow the operator to control the heat inactivation process by controlling the flow rate of the sample through the heat exchanger, thus controlling the duration of the heating process, and the temperature of the heat exchanger, thus controlling the temperature of heat inactivation.

Alternatively, heat inactivation may be accomplished using batch systems of various sizes. For example, heat inactivation may be accomplished at the 1 L scale, by placing the AAV-containing sample in a 1 L PETG bottle and placing the bottle in a water bath set at the desired inactivating temperature for the desired period of time, with mixing; for example, the samples may be heated to 47° C. for 20 minutes. At a larger scale, heat inactivation may be accomplished by placing the rAAV-containing sample in a 5 L bioprocessing bag on a temperature controlled rocking platform set at the desired inactivating temperature, for the desired period of time. For example, the rocking platform may be set to 49° C. at a rocking speed of 30 RPM, with a 12° angle of mixing for 40 minutes.

Heat inactivation may occur at any temperature where there is a sufficient difference in stability between rAAV particles and helper virus particles that helper virus particles are substantially inactivated while active rAAV particles remain. A person of skill in the art will understand that higher temperatures may be required to achieve greater levels of AV reduction. In some embodiments, the heat inactivation step includes the use of a buffer containing kosmotropic salts and/or divalent or trivalent cations. Methods of heat inactivation in the presence of a buffer containing kosmotropic salts and/or divalent or trivalent cations is described in WO/2017/172772.

Once heat inactivation has been accomplished, it may be necessary or desirable to determine the efficiency of inactivation. The efficacy of an inactivation protocol is determined by assays that detect the presence of replication competent helper virus, such as a plaque assay. Plaque assays for helper virus are well known to those in the art, including plaque assays for AV, HSV, baculovirus, and others. Plaque assays of adenovirus may be conducted using any appropriate cell type, for example HeLa or HEK293 cells. Standard plaque assay protocols are described in, for example, Current Protocols in Human Genetics, 2003. Alternative assays for measuring adenoviral titers include those that allow the identification of infected cells in culture by detecting viral proteins, such as hexon proteins, using immunocytochemical staining. Such assays include the QuickTiter™ Adenovirus Titer Immunoassay Kit (Cell Biolabs, San Diego, CA). The efficiency of inactivation is generally reported as the log reduction of virus (LRV).

Quantification of rAAV particles is complicated by the fact that AAV infection does not result in cytopathic effect in vitro, and therefore plaque assays cannot be used to determine infectious titers. AAV particles can be quantified using a number of methods, however, including quantitative polymerase chain reaction (qPCR) (Clark et al., Hum. Gene Ther. 10, 1031-1039 (1999)) or dot-blot hybridization (Samulski et al., J. Virol. 63, 3822-3828 (1989)), or by optical density of highly purified vector preparations (Sommer et al., Mol. Ther. 7, 122-128 (2003)). DNase-resistant particles (DRP) can be quantified by real-time quantitative polymerase chain reaction (qPCR) (DRP-qPCR) in a thermocycler (for example, an iCycler iQ 96-well block format thermocycler (Bio-Rad, Hercules, CA)). Samples containing AAV particles are incubated in the presence of DNase I (100 U/ml; Promega, Madison, WI) at 37° C. for 60 min, followed by proteinase K (Invitrogen, Carlsbad, CA) digestion (10 U/ml) at 50° C. for 60 min, and then denatured at 95° C. for 30 min. The primer-probe set used should be specific to a non-native portion of the AAV vector genome, for example, the poly(A) sequence of the protein of interest. The PCR product can be amplified using any appropriate set of cycling parameters, based on the length and composition of the primers, probe, and amplified sequence. Alternative protocols are disclosed in, for example, Lock et al., Human Gene Therapy Methods 25 (2): 115-125 (2014).

The infectivity of rAAV particles can be determined using a $TCID_{50}$ (tissue culture infectious dose at 50%) assay, as described for example in Zhen et al., Human Gene Therapy 15:709-715 (2004). In this assay, AAV vector particles are serially diluted and used to co-infect a Rep/Cap-expressing cell line along with AV particles in 96-well plates. 48 hours post-infection, total cellular DNA from infected and control wells is extracted. AAV vector replication is then measured using qPCR with transgene-specific probe and primers. $TCID_{50}$ infectivity per milliliter ($TCID_{50}$/ml) is calculated with the Kärber equation, using the ratios of wells positive for AAV at 10-fold serial dilutions.

IV. Recombinant AAV for Gene Therapy

AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORB). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Days and Berns, *Clin Microbiol Rev* 21 (4): 583-593, 2008).

The left ORF of AAV contains the Rep gene, which encodes four proteins-Rep78, Rep68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21 (4): 583-593, 2008).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev,* 21 (4): 583-593, 2008).

Methods for producing rAAV suitable for gene therapy are well known in the art (see, for example, U.S. Patent Application Nos. 2012/0100606; 2012/0135515; 2011/0229971; and 2013/0072548; and Ghosh et al., *Gene Ther* 13 (4): 321-329, 2006), and can be utilized with the recombinant nucleic acid molecules and methods disclosed herein.

Compositions comprising the rAAV disclosed herein and a pharmaceutically acceptable carrier are provided by the present disclosure. Suitable pharmaceutical formulations for administration of rAAV can be found, for example, in U.S. Patent Application Publication No. 2012/0219528. The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In some embodiments, the rAAV is formulated in a buffer/carrier suitable for infusion in human subjects. The buffer/carrier should include a component that prevents the rAAV from sticking to the infusion tubing but does not interfere with the rAAV binding activity in vivo. Various suitable solutions may include one or more of: a buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene 10 (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol.

The current invention also provides methods of treating a subject diagnosed with a glycogen storage disease type 1a (GSD-Ia) and administering to the subject a therapeutically effective amount of an rAAV (or a composition comprising the rAAV) disclosed herein.

Any suitable method or route can be used to administer an rAAV or an rAAV-containing composition described herein. Routes of administration include, for example, systemic, oral, inhalation, intranasal, intratracheal, intraarterial, intraocular, intravenous, intramuscular, subcutaneous, intradermal, and other parental routes of administration. In some embodiments, the rAAV or the composition comprising rAAVs are administered intravenously.

The specific dose administered can be a uniform dose for each patient, for example, $1.0 \times 10^{13}$-$1.0 \times 10^{15}$ genome copies (GC) of virus per patient. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. For example, the optimal biological dose of the rAAV administered may be identified by assessing the time (in minutes) to first hypoglycemic event (defined as glucose <60 mg/dL (<3.33 mmol/L) during a controlled fasting challenge, which will end when either hypoglycemia occurs or 15 hours is reached. An individual patient's dosage can also be adjusted as the progress of the disease is monitored.

In some embodiments, the rAAV is administered at a dose of, e.g., about $1.0 \times 10^{11}$ genome copies per kilogram of patient body weight (GC/kg) to about $1 \times 10^{14}$ GC/kg, about $5 \times 10^{11}$ genome copies per kilogram of patient body weight (GC/kg) to about $5 \times 10^{13}$ GC/kg, or about $1 \times 10^{12}$ to about $1 \times 10^{13}$ GC/kg, as measured by qPCR or digital droplet PCR (ddPCR). In some embodiments, the rAAV is administered at a dose of about $2 \times 10^{12}$ GC/kg. In some embodiments, the rAAV is administered at a dose of about $6 \times 10^{12}$ GC/kg. In some embodiments, the rAAV is administered at a dose of about $1 \times 10^{13}$ GC/kg. The rAAV can be administered in a single dose, or in multiple doses (such as 2, 3, 4, 5, 6, 7, 8, 9, 10 or more doses) as needed for the desired therapeutic results.

Doses may be given once or more times weekly, monthly or yearly, or even once every 2 to 20 years. For example, each dose may be given at minimum of 1 week apart, 2 weeks apart, 3 weeks apart, a month apart, 3 months apart, 6 months apart, or 1 year apart. Persons of ordinary skill in the art can easily estimate repetition rates for dosing based on measured residence times and concentrations of the targetable construct or complex in bodily fluids or tissues.

V. Methods of Increasing Recombinant Viral Yield and Gene Therapy Efficacy

The current invention also provides a method of increasing the yield of a recombinant virus from host cells, wherein the method comprises removing one or more Alu elements or Alu element-related sequences from a recombinant viral vector. In some embodiments, the Alu element-related sequence is at least 50% identical to an Alu element, for example, selected from the contiguous nucleotides 934-1127 (Alu-1), 1488-1823 (Alu-2), and 1995-2350 (Alu-3) of SEQ ID NO: 6. The recombinant viral vector can be, for example, a lentivirus vector, a retrovirus vector, an adenovirus vector, or an adeno-associated virus (AAV) vector. In some embodiments, one or more Alu elements or Alu element-related sequences is removed from a promoter/enhancer region within the viral vector. In some embodiments, one or more Alu elements or Alu element-related sequences is removed from an intron region within the viral vector. In some embodiment, removal of the Alu element(s) or Alu element-related sequences reduces self-complementary structures formed during packaging of the recombinant viral particles, and thus improve the viral yield form host cells.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including" is intended merely to illustrate better the present invention and does not pose a limitation on the scope of the invention unless claimed. No language in the specification should be construed as indicating any non-claimed element as essential to the practice of the present invention.

EXAMPLES

The invention now being generally described, will be more readily understood by reference to the following examples, which are included merely for purposes of illustration of certain aspects and embodiments of the present invention, and is not intended to limit the invention.

Example 1—AAV Vectors and rAAV Produced from the Vectors

AAV vector

An AAV vector was constructed including a G6PC expression cassette bounded by two AAV2 inverted terminal repeats (ITRs, SEQ ID NO: 15). The G6PC expression cassette was defined at its G6PC promoter/enhancer (GPE) 5' end by the primer sequence "1S" listed in Yiu et al., 2010, *Molecular Therapy* 18 (6): 1076-84 and its associated KpnI restriction endonuclease site. The G6PC expression cassette was defined at its SV40 late polyadenylation signal 3' end by alignment with the SV40 genome and an associated SalI restriction endonuclease site. All G6PC expression cassettes contain a GPE, an intron, a codon optimized human G6PC gene, and an SV40 late poly A tail as illustrated in FIG. 1A. Different versions of the G6PC expression cassettes were created, each of which either contains a wild-type GPE, or a modified GPE as illustrated in FIG. 1B. Elements of the G6PC expression cassettes are described below.

The wild-type G6PC promoter/enhancer (GPE, SEQ ID NO: 6) is from the *Homo sapiens*, and defined by RefSeq NG_011808. This sequence is the endogenous promoter for human G6PC gene, and has almost exclusive activity in the liver and minimal activity in the kidney. The wild-type GPE contains 3 Alu elements, located at the contiguous nucleotides 934 1127 (Alu-1), 1488-1823 (Alu-2) and 1995-2350 (Alu-3) of SEQ ID NO: 6. The AAV vector DTC161 contains a G6PC expression cassette comprising the wild-type GPE. The AAV vector DTC175 contains a G6PC expression cassette comprising a GPE with a deletion of the Alu-1 and Alu-2 sequences. The AAV vector DTC176 contains a G6PC expression cassette comprising a GPE in which the orientations of the Alu-1 and Alu-2 sequences are reversed. The AAV vector DTC177 (represented by SEQ ID NO: 1) contains a G6PC expression cassette comprising a GPE with a deletion of the Alu-1, Alu-2, and Alu-3 sequences. The AAV vector DTC178 contains a G6PC expression cassette comprising a GPE with a deletion of the Alu-3 sequence. The AAV vector DTC179 contains a G6PC expression cassette comprising a GPE in which the orientation of the Alu-3 sequence is reversed.

The chimeric intron (SEQ ID NO: 13) is composed of the 5'-donor site from the first intron of the human β-globin gene and the branch and 3'-acceptor site from the intron of an immunoglobulin gene heavy chain variable region. The sequences of the donor and acceptor sites, along with the branchpoint site, have been changed to match the consensus sequences for splicing (CI-neo Mammalian Expression Vector Technical Bulletin TB215, Promega Life Sciences Corporation). The purpose of the chimeric intron is to improve gene expression.

The G6PC cDNA (SEQ ID NO: 4) is from *Homo sapiens*, and is codon optimized for expression in human cells. Codon optimization was performed on human G6PC cDNA using proprietary OptimumGene™ codon optimization technology (GenScript, Piscataway, NJ). The optimized cDNA sequences were examined and further modified to eliminate potential alternative reading frames (ARFs) from internal non-in-frame ATG sequences that could theoretically encode peptides of 9 or more amino acids in length. For example, a codon optimized G6PC cDNA is represented by SEQ ID NO: 3.

The Simian virus 40 (SV40) late polyadenylation signal (Genbank #J02400, SEQ ID NO: 14) provides a cis sequence for efficient polyadenylation of the G6PC mRNA. This element functions as a signal for a specific cleavage event at the 3' end of the nascent transcript and addition of a long polyadenyl tail.

Figure 2:
FIG. 2 is a schematic representation of an exemplary AAV vector (DTC161), with various key components shown therein.

Each G6PC expression cassette was cloned into an AAV vector. All AAV vectors had a backbone encoding the kanamycin-resistance gene. An AAV vector DTC161 (pDTX.hG6PCco.401) is illustrated in FIG. 2 as an example.

rAAV Virions

The AAV vector genome is a single-stranded DNA genome. Only the sequences between and inclusive of the ITR sequences are packaged into the AAV virion. Virions were produced by transfection of three plasmids into human embryonic kidney 293 (HEK293) cells, which provide E1a and E1b gene products. The first plasmid is the AAV vector described herein. The second plasmid is pAAV2-8.KanR (p2123-FH), a packaging plasmid containing the wild-type AAV2 rep and AAV8 cap genes. The third plasmid is pAdDeltaF6 (Kan), a helper adenovirus plasmid.

Figure 3:
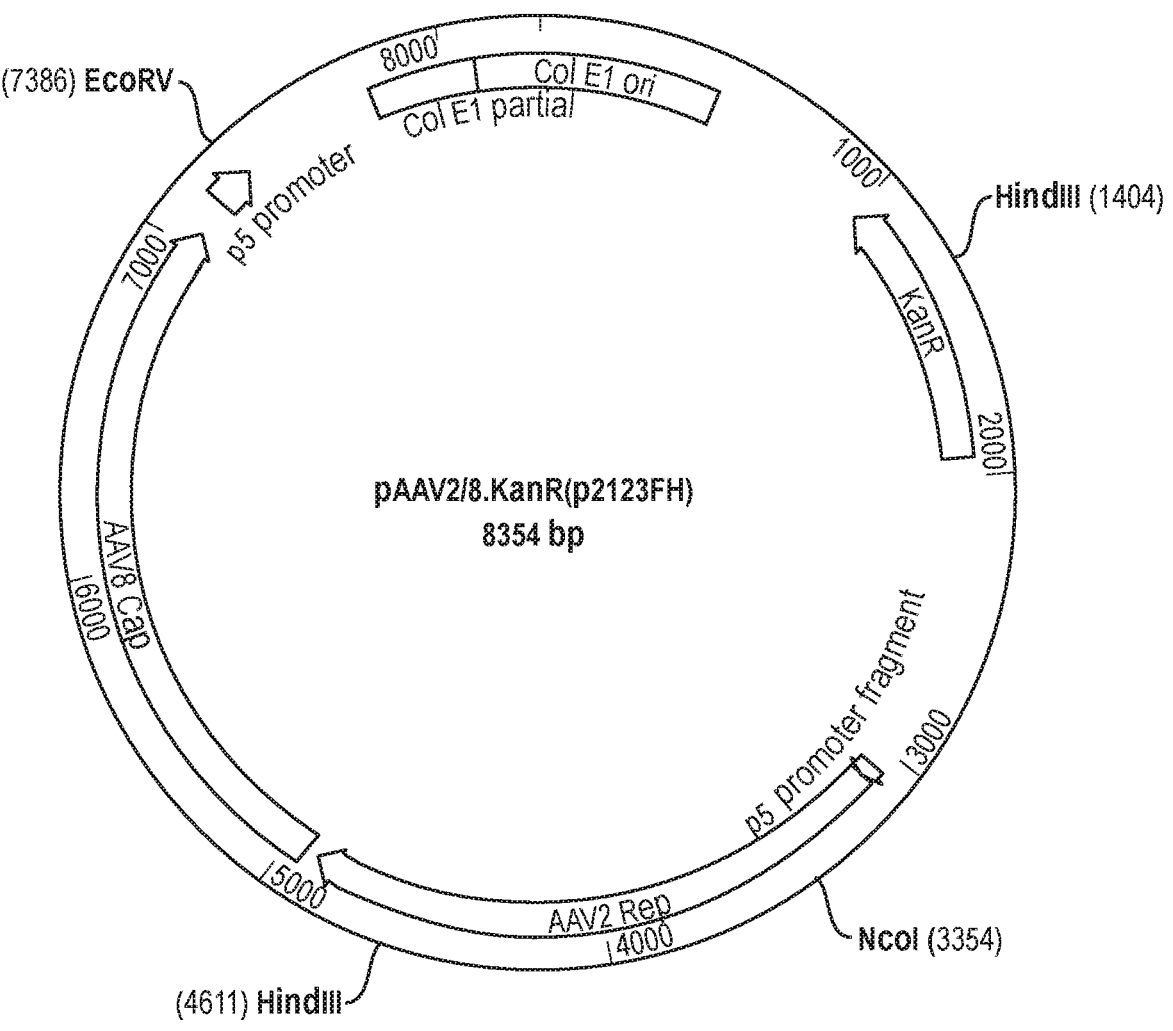
FIG. 3 is a schematic representation of pAAV2-8.KanR (p2123-FH) AAV Rep/Cap plasmid, which provides Rep and Cap function in packaging rAAV when co-transfected with AAV vectors into host cells.

The adeno-associated Rep/Cap plasmid pAAV2/8.KanR (p2123-FH) (8354 bp) encodes the four wild-type AAV2 viral replication (Rep) proteins and the three wild-type AAV VP capsid (cap) proteins from serotype 8. An illustration of the pAAV2/8.KanR (p2123-FH) plasmid is shown in FIG. 3. Within the plasmid, the AAV p5 promoter that normally drives Rep gene expression has been moved from the 5' end of the Rep region to the 3' end of the AAV8 cap region. This arrangement introduces a spacer between the promoter and the Rep gene (i.e., the plasmid backbone) resulting in down-regulation of the expression of Rep and an increase in the ability to support high titer rAAV production. The gene for kanamycin resistance and the MB1 origin are included for plasmid production in *E. coli.*

Figure 4:
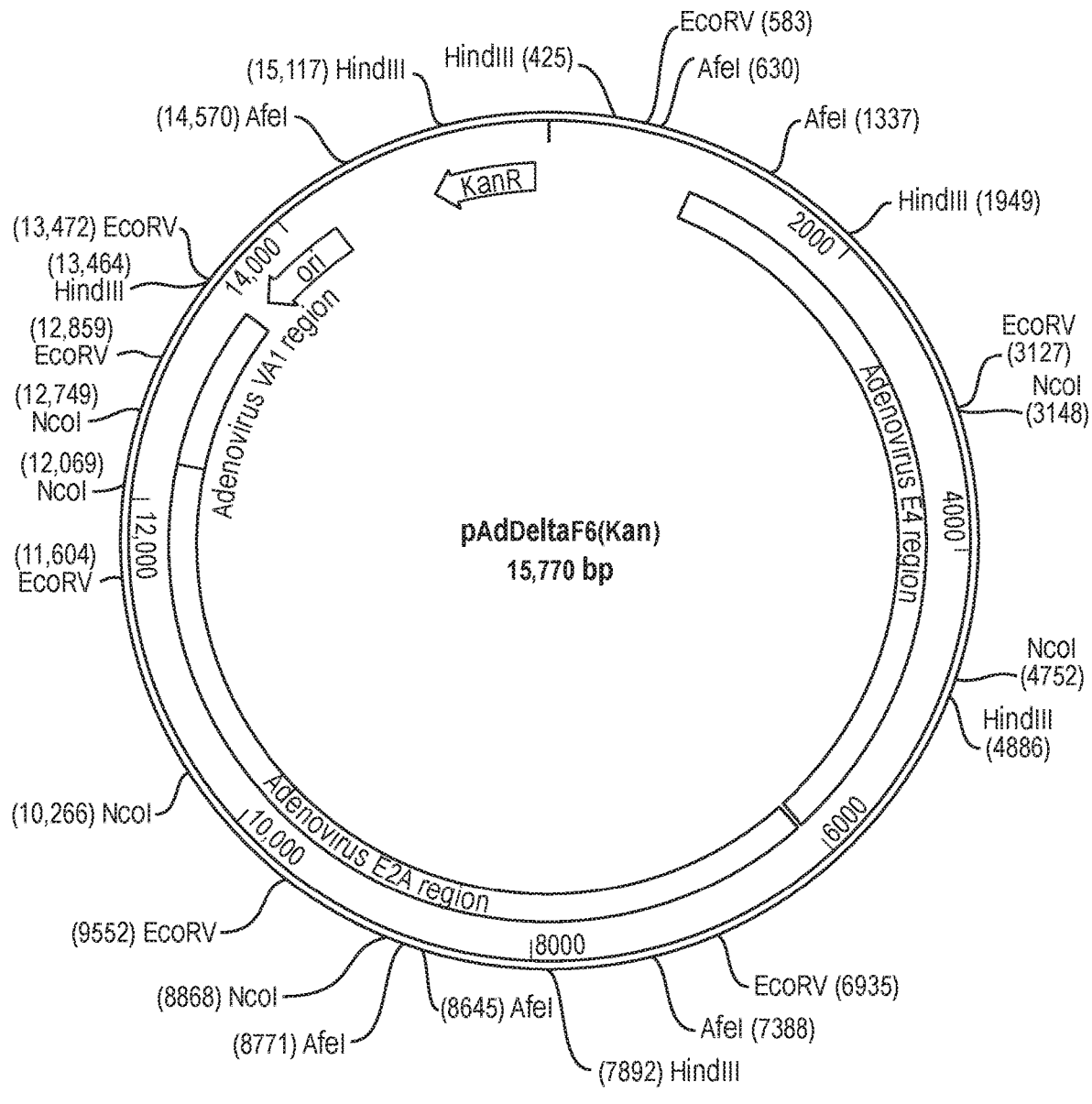
FIG. 4 is a schematic representation of pAdDeltaF6 (Kan) adenovirus helper plasmid for rAAV production when co-transfected with AAV vectors and Rep/Cap plasmids into host cells.

The plasmid pAdDeltaF6 (Kan) contains the regions of the adenovirus genome that are important for AAV replication, namely E2A, E4, and VA RNA (FIG. 4). The adenovirus E1 functions are also required but are provided by the HEK293 host cells. The plasmid does not contain other adenovirus replication, structural genes, or the cis elements critical for adenovirus replication such as the adenoviral ITRs and therefore, no infectious adenovirus is expected to be generated. The gene for kanamycin resistance and the MB1 origin are included for plasmid production in *E. coli*.

Example 2—Deletion of Alu Elements Improves rAAV Yield

AAV vectors containing the wild-type GPE or a modified GPE were used to transfect HEK293 cells with the Rep/Cap plasmid and the helper plasmid described above.

The modified GPE contains either deleted Alu elements (in DTC175, DTC177, and DTC178 vectors) or reversed Alu elements in direction (in DTC176 and DTC179 vectors). DTC175 viral vector comprises a G6PC expression cassette comprising a GPE with a deletion of the Alu-1 and Alu-2 sequences, DTC176 viral vector comprises a G6PC expression cassette comprising a GPE in which all three Alu elements are present but the orientations of the Alu-1 and Alu-2 sequences are reversed, DTC177 viral vector comprises a G6PC expression cassette comprising a GPE with a deletion of the Alu-1, Alu-2 and Alu-3 sequences, DTC178 viral vector comprises a G6PC expression cassette comprising a GPE with a deletion of the Alu-3 sequence, and DTC179 viral vector comprises a G6PC expression cassette comprising a GPE in which all three Alu elements are present but the orientation of the Alu-3 sequence is reversed).

Figure 5:
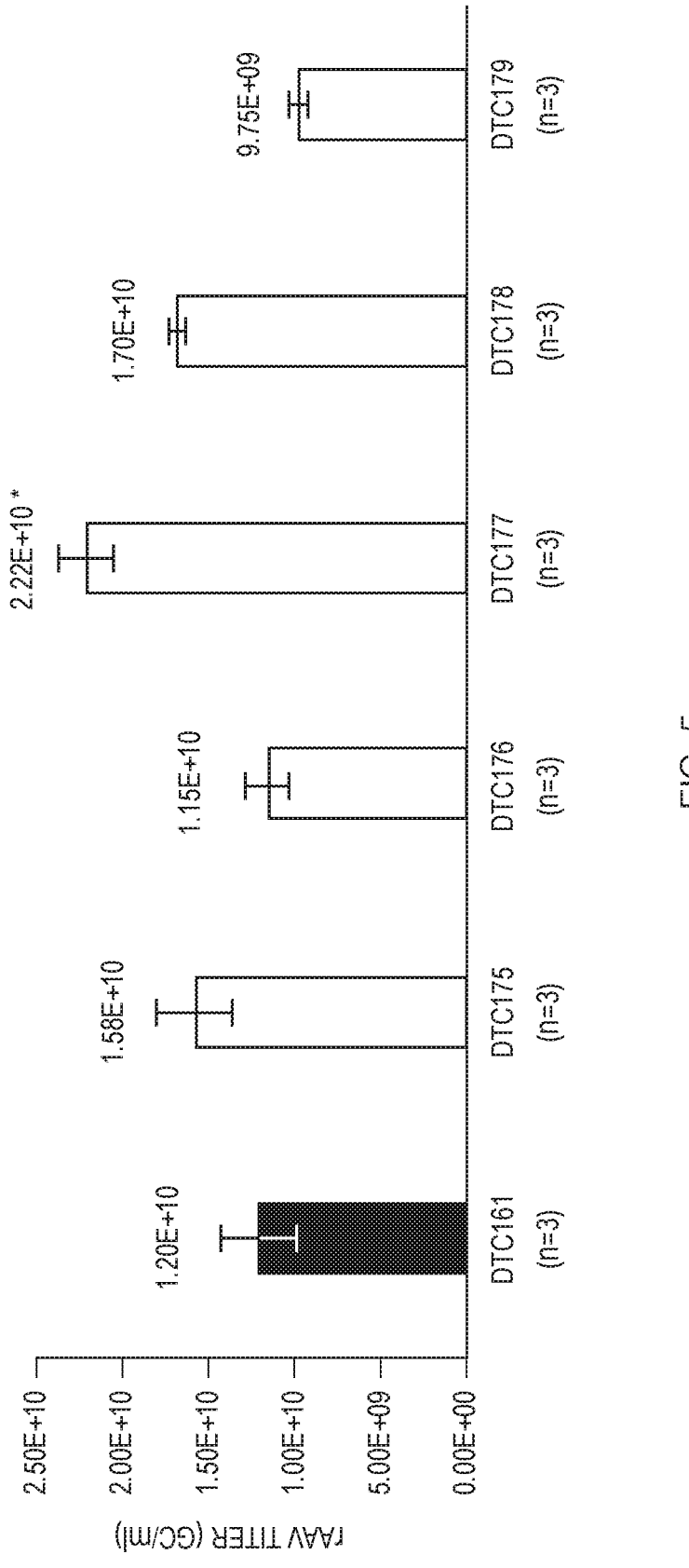
FIG. 5 is a bar graph showing titers of rAAV produced from host cells after transfection of various AAV vectors. Three tests were performed under each condition, and standard deviations were shown. * indicates $P < 0.05$ in comparison with DTC161.
Figure 6:
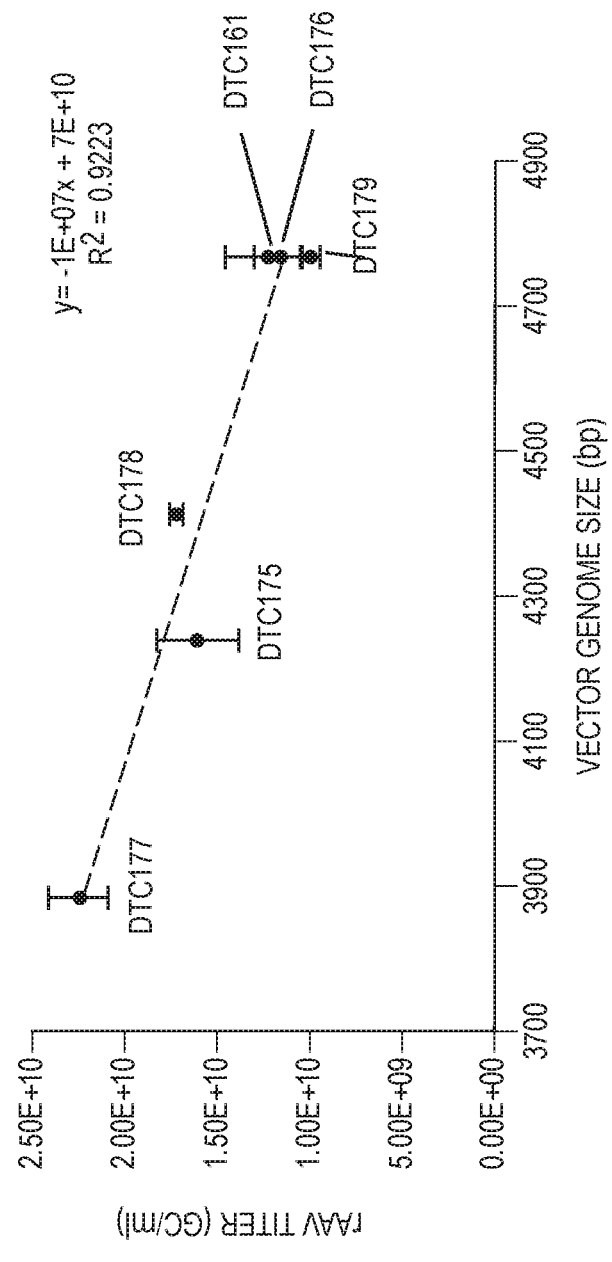
FIG. 6 is a graph showing titers of rAAV produced plotted as a function of vector genome size.

On day 5 after co-transfection, the infected cells were lysed for 2 hours at 37° C. in the lysis buffer containing sodium deoxycholate and Benzonase®. Supernatant from the samples were then sequentially digested with DNase I and Proteinase K to liberate rAAV genomic DNA. TaqMan qPCR amplifying the BGH-PolyA coding region of the AAV vector was then used to determine the rAAV genome copy number (GC) based on an rAAV plasmid standard curve. FIG. 5 is a bar graph showing titers of rAAV produced from host cells after transfection of various AAV vectors. FIG. 5 shows rAAV titers measured by qPCR, and suggests that deletion of one or more of the Alu elements from the GPE (in DTC175, DTC177, and DTC178 vectors) significantly increased rAAV yield in comparison with DTC161, which contains the wild-type GPE. However, reversal of one or more of the Alu elements (in DTC176 and DTC179 vectors) did not improve rAAV yield in comparison with DTC161. Quantification of the viral yield is summarized in Table 1. As shown in Table 1, deletion of one or more Alu elements from the GPE significantly improves the rAAV yield. A second analysis showing titers of rAAV produced plotted as a function of vector genome size is presented as a graph in FIG. 6. FIG. 6 shows that the vector genome having the smallest size, DTC177 (represented by SEQ ID NO: 1), produced the highest titers.

TABLE 1

Quantification summary of the viral yields produced from HEK293 cells after transfection of AAV vectors (DTC161, DTC175, DTC176, DTC177, DTC178, or DTC179).

| Sample Name | Alu Content | Genome Size (bp) | Raw Yield (fold over DTC161) | Average GC/mL Post-Affinity Chromatography (fold over DTC161) |
|---|---|---|---|---|
| DTC161 | All 3 | 4768 | 1.20e10 | 4.72E+12 |
| DTC175 | 1 + 2 deletion | 4238 | 1.58e10 (1.3) | 9.50E+12 (2.0) |
| DTC176 | All 3 | 4768 | 1.15e10 (0.9) | 4.95E+12 (1.1) |
| DTC177 | 1 + 2 + 3 deletion | 3882 | 2.22e10 (1.9) | 9.75E+12 (2.1) |

TABLE 1-continued

Quantification summary of the viral yields produced from HEK293 cells after transfection of AAV vectors (DTC161, DTC175, DTC176, DTC177, DTC178, or DTC179).

| Sample Name | Alu Content | Genome Size (bp) | Raw Yield (fold over DTC161) | Average GC/mL Post-Affinity Chromatography (fold over DTC161) |
|---|---|---|---|---|
| DTC178 | 3 deletion | 4412 | 1.70e10 (1.4) | 8.22E+12 (1.7) |
| DTC179 | All 3 | 4768 | 0.98e10 (0.8) | 3.56E+12 (0.8) |

Example 3—Deletion of Alu Elements Improves rAAV Packaging

In order to assess whether deletion of one of more of Alu elements impacts packaging of the rAAVs, the rAAVs produced as described in Example 2 were harvested and total DNA was isolated from each rAAV (produced from a control viral vector, DTC161, DTC175, DTC176, DTC177, DTC178, or DTC179). Approximately, $7.12 \times 10^{10}$ total amount of each rAAV GC was subjected to agarose gel electrophoresis, and subsequently stained with SYBR Gold. Control viral vector used in this experiment was AAV8-LSP-hFIXco3-WPRE-pA (generated at Virovek, custom purification, catalog/lot #150282 of 061015), which provided known DNA size migration on the gel, and confirmation that the experimental method was able to disrupt the integrity of AAV capsid and release packaged DNA.

Figure 7:
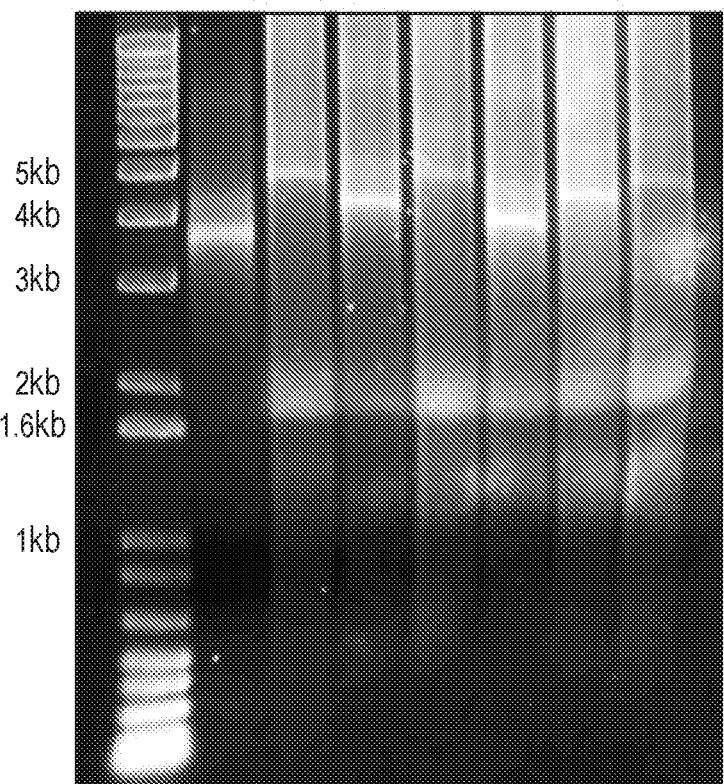
FIG. 7 is an image of an agarose gel, which shows bands of released DNA, evaluating capsid degradation and ability to release packaged DNA, when the full-length DNA isolated from rAAVs of a control viral vector, DTC161, DTC175, DTC176, DTC177, DTC178, and DTC179 are subjected to an agarose gel electrophoresis. The full length viral DNAs are between 3.8 kb-5 kb. '*' denotes capsid degradation and intact genome of full-length DNA isolated from the control viral vector upon treatment with sodium dodecyl sulfate (SDS).

As shown in FIG. 7, full length viral DNAs were between 3.8 kb-5 kb. '*' denotes capsid degradation and intact genome of full-length DNA isolated from the control viral vector upon treatment with sodium dodecyl sulfate (SDS).

Figures 8A, 8B:
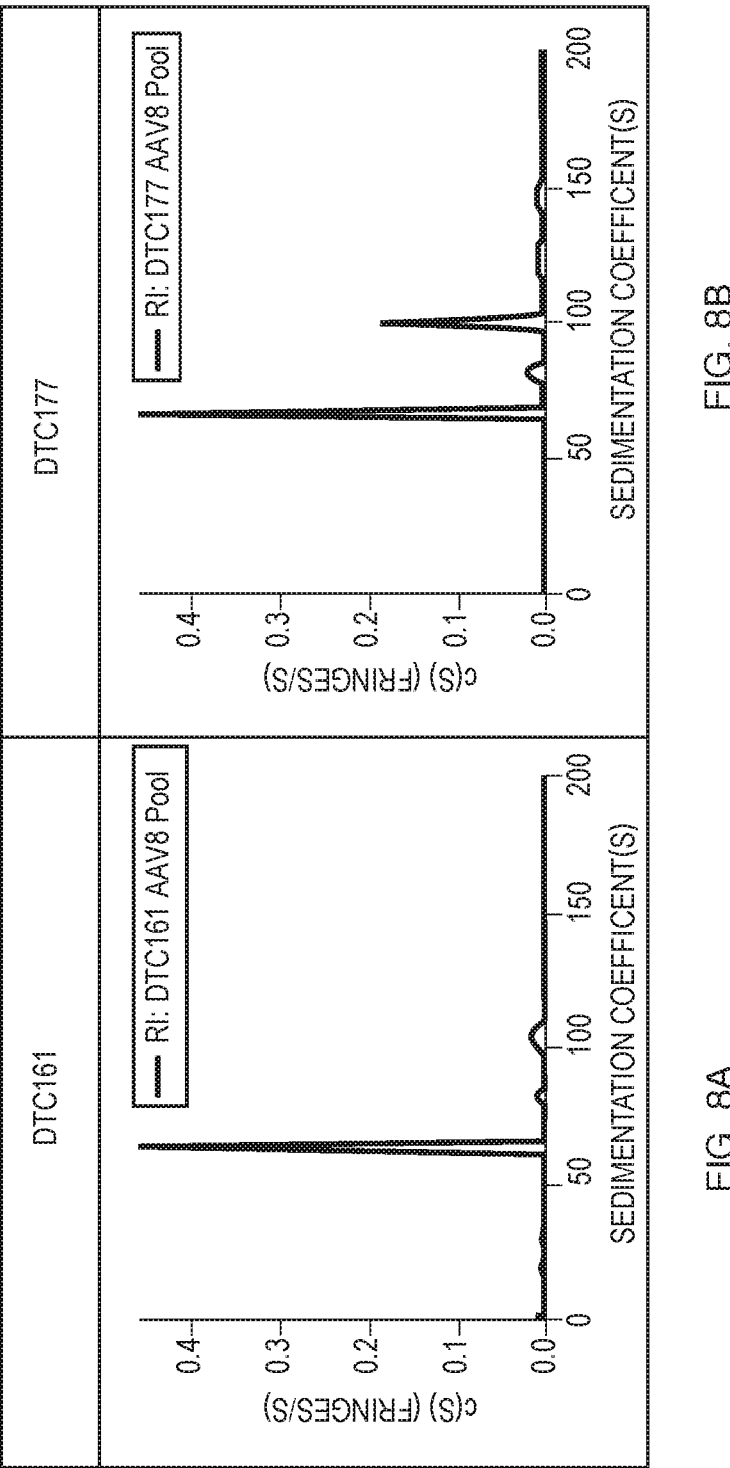
FIG. 8A is a graph showing analytical ultracentrifuge traces of particle densities from DTC161 vector preparation produced in HEK293 cells.
FIG. 8B is a graph showing analytical ultracentrifuge traces of particle densities from a DTC177 vector (represented by SEQ ID NO: 1) preparation produced in HEK293 cells. Abbreviations used: RI-refractive index.

Higher staining intensity of full-length DNA isolated from rAAVs of DTC177, DTC175, and DTC178 where one or more Alu elements were deleted from GPE was observed (see FIG. 7). This result suggests that deletion of at least one Alu element improves rAAV packaging of full-length viral genome. Moreover, analytical ultracentrifuge traces of DTC161 and DTC177 particles analyzed for empty (appearing at approximately 60S) and full vector DNA-containing particles (appearing at approximately 100S), respectively demonstrated that the construct with the Alu elements deleted produced a higher percentage of full particles (see FIGS. 8A-8B). FIG. 8A is a graph showing analytical ultracentrifuge traces of particle densities from DTC161 vector preparation produced in HEK293 cells. FIG. 8B is a graph showing analytical ultracentrifuge traces of particle densities from DTC177 vector (represented by SEQ ID NO: 1) preparation produced in HEK293 cells.

These data indicate improved packaging occurs in vectors lacking Alu sequences.

Figures 9A, 9B:
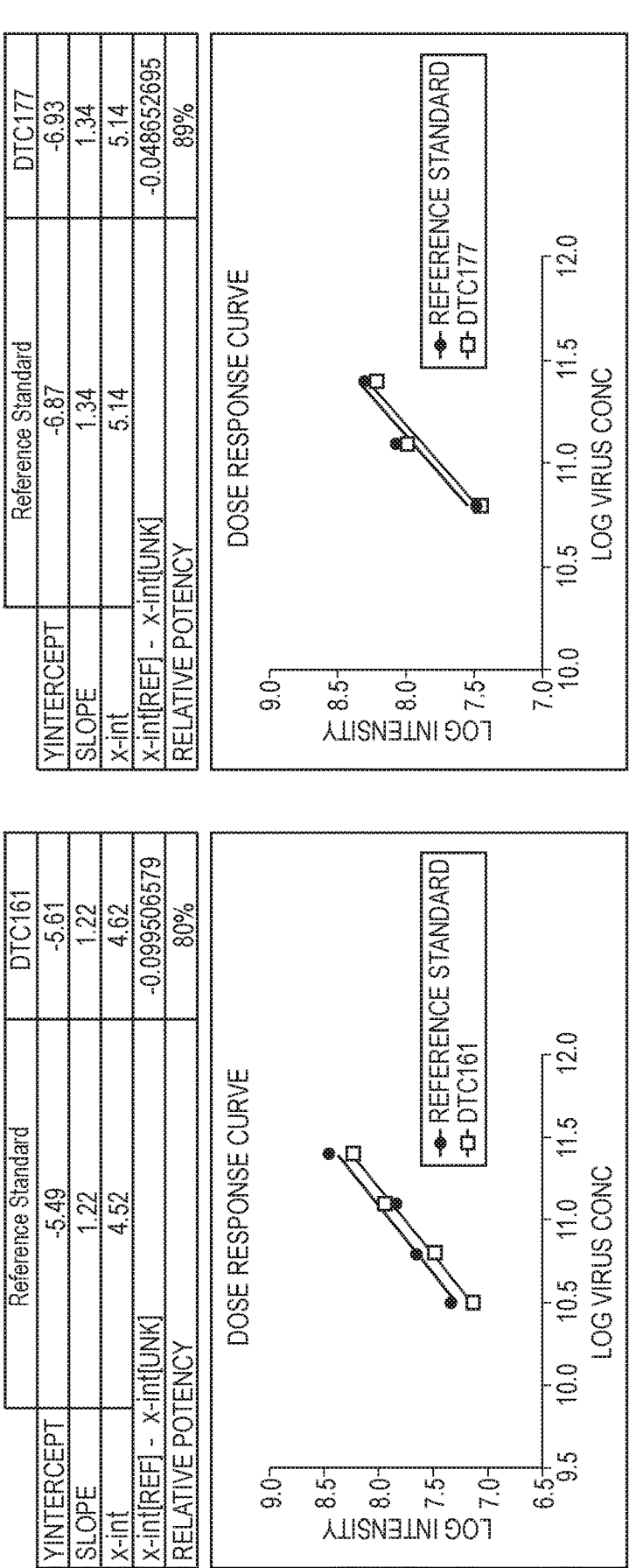
FIG. 9A is a dose-response curve for induced G6Pase-α expression after infection with rAAV derived from DTC161 vector.
FIG. 9B is a dose-response curve for induced G6Pase-α expression after infection with rAAV derived from DTC177 vector (represented by SEQ ID NO: 1). X axis indicates rAAV doses used to infect HuH7 liver cells. Y axis indicates the induced G6PC mRNA expression in the cells. rAAV derived from a development batch-produced DTC161 vector was used as a reference standard. Abbreviations used: REF-Reference standard; UNK-test sample.

Example 4—Deletion of Alu Elements in GPE does not Affect the Promoter Potency In order to assess whether deletion of one or more of the Alu elements impacts the potency of GPE to direct G6PC gene expression in vivo, rAAVs derived from different vectors (shown in Table 2) were used to infect HuH7 liver cells. After 48 hours of infection, cells were lysed and total mRNA was harvested. G6PC mRNA expression was analyzed by quantitative RT-PCR. FIGS. 9A-9B show exemplary dose response curves between the rAAV dose and G6PC mRNA expression level in HuH7 liver cells for rAAVs derived from DTC161 and DTC177 (represented by SEQ ID NO: 1). FIG. 9A is a dose-response curve for induced G6Pase-α expression after infection with rAAV containing DTC161. FIG. 9B is a dose-response curve for induced G6Pase-α expression after infection with rAAV containing DTC177 (represented by SEQ ID NO: 1). To calculate relative potency of a test sample, the RNA values (genome copies per μg of total RNA) at each multiplicity of infection (MOI) for both reference standard (rAAV derived from a development batch-produced DTC161 vector) and the test sample were added to a GraphPad Prism file template. The template uses a log-log transformation of the data and a linear fit that is constrained so that the curves have a shared slope. The Y axis corresponds to the RNA values, and the X axis corresponds to the MOI of the sample. The Y Intercept and Slope data generated by the GraphPad Prism template were used to determine the X Intercepts of the reference standard and the test sample by implementing the following formula: X Int=(0−[Y Intercept])/Slope. The final relative potency value is determined by comparing the X intercepts utilizing the following formula: $10^{\{[X\ Intercept\ Reference]-[X\ Intercept\ Sample]\}}$.

TABLE 2

Summary of relative potency of GPE in each rAAV sample.

| Sample | Relative Potency |
|---|---|
| DTC-161 | 80% |
| DTC-175 | 83% |
| DTC-176 | 79% |
| DTC-177 | 89% |
| DTC-178 | 75% |
| DTC-179 | 85% |

This result suggests that deletion of one or more of Alu elements in GPE (in DTC175, DTC177, and DTC178 vectors) does not compromise the potency of the GPE to drive G6PC gene expression in vivo.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a," "an," and "the" include plural reference unless the context clearly dictates otherwise. As well, the terms "a" (or "an"), "one or more," and "at least one" can be used interchangeably herein. It is also to be noted that the terms "comprises," "comprising," "containing," "including," and "having" can be used interchangeably.

Without further elaboration, it is believed that one skilled in the art can, based on the above description, utilize the present invention to its fullest extent. The specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A recombinant nucleic acid molecule comprising a modified G6PC promoter/enhancer (GPE) sequence, wherein the modified GPE sequence has a deletion of one or more Alu element(s) selected from the group consisting of Alu-1, Alu-2, and Alu-3, wherein:

the modified GPE sequence comprises the nucleic acid sequence of contiguous nucleotides 146-2123 of SEQ ID NO: 1, or the nucleic acid sequence of SEQ ID NO: 7, 8, 9, 10, 11, or 12.

2. The recombinant nucleic acid molecule of claim 1 further comprising a glucose-6-phosphatase-alpha (G6Pase-α) coding sequence.

3. The recombinant nucleic acid molecule of claim 2, wherein the G6Pase-α coding sequence comprises a sequence identical to SEQ ID NO: 3 or SEQ ID NO: 4.

4. The recombinant nucleic acid molecule of claim 2, wherein the recombinant nucleic acid molecule further comprises a polyadenylation (polyA) signal sequence and/or an intron.

5. The recombinant nucleic acid molecule of claim 2, wherein the recombinant nucleic acid molecule comprises SEQ ID NO: 1 or SEQ ID NO: 2.

6. A recombinant vector comprising the recombinant nucleic acid molecule of claim 2.

7. The recombinant vector of claim 6, wherein the recombinant vector is an adeno-associated virus (AAV) vector.

8. The recombinant vector of claim 7, wherein the AAV vector is an AAV serotype 8 (AAV8) vector.

9. An isolated host cell comprising the recombinant nucleic acid molecule of claim 2.

10. A method of increasing recombinant AAV (rAAV) yield, comprising delivering the recombinant vector of claim 7 to a eukaryotic host cell culture and harvesting the rAAV from the eukaryotic host cell culture.

11. A composition comprising the recombinant vector of claim 7 and a pharmaceutically acceptable carrier.

12. A recombinant adeno-associated virus (rAAV) for the treatment of glycogen storage disease type Ia (GSD-Ia), said rAAV comprising an AAV capsid and a vector genome packaged therein, said vector genome comprising:

(a) an AAV 5' inverted terminal repeat sequence (ITR) sequence;

(b) a promoter/enhancer sequence comprising the contiguous nucleotides 146-2123 of SEQ ID NO: 1;

(c) a coding sequence encoding a glucose-6-phosphatase alpha (G6Pase-α); and (d) an AAV 3' ITR.

13. The rAAV of claim 12, wherein the G6Pase-α comprises an amino acid sequence at least 90% identical to SEQ ID NO: 5 and/or the coding sequence encoding the G6Pase-α is at least 90% identical to SEQ ID NO: 3 or SEQ ID NO: 4.

14. The rAAV of claim 13, wherein the AAV capsid is an AAV8 capsid.

15. The recombinant nucleic acid molecule of claim 2, wherein the G6Pase-α coding sequence is at least 95% identical to the amino acid sequence of SEQ ID NO: 3 or SEQ ID NO: 4.

* * * * *